(12) United States Patent
Ho et al.

(10) Patent No.: US 10,450,598 B2
(45) Date of Patent: Oct. 22, 2019

(54) SYSTEMS AND METHODS FOR OBTAINING A DROPLET HAVING A DESIGNATED CONCENTRATION OF A SUBSTANCE-OF-INTEREST

(71) Applicant: Illumina, Inc., San Diego, CA (US)

(72) Inventors: Hwai-En Ho, San Diego, CA (US); Gregory F. Smith, Cary, NC (US); Rahul R. Dhopeshwarkar, Escondido, CA (US)

(73) Assignee: ILLUMINA, INC., San Diego, CA (US)

( * ) Notice: Subject to any disclaimer, the term of this patent is extended or adjusted under 35 U.S.C. 154(b) by 305 days.

(21) Appl. No.: 15/259,310

(22) Filed: Sep. 8, 2016

(65) Prior Publication Data

US 2017/0073729 A1    Mar. 16, 2017

Related U.S. Application Data

(60) Provisional application No. 62/217,199, filed on Sep. 11, 2015, provisional application No. 62/253,488, filed on Nov. 10, 2015.

(51) Int. Cl.
*G01N 33/48* (2006.01)
*C12Q 1/6806* (2018.01)
*B01L 3/00* (2006.01)
*G06G 7/58* (2006.01)

(52) U.S. Cl.
CPC ...... *C12Q 1/6806* (2013.01); *B01L 3/502792* (2013.01); *B01L 2300/0867* (2013.01); *B01L 2400/0427* (2013.01)

(58) Field of Classification Search
None
See application file for complete search history.

(56) References Cited

U.S. PATENT DOCUMENTS

| 6,172,218 | B1 | 1/2001 | Brenner |
| 6,210,891 | B1 | 4/2001 | Nyren et al. |
| 6,258,568 | B1 | 7/2001 | Nyren |
| 6,274,320 | B1 | 8/2001 | Rothberg et al. |
| 6,306,597 | B1 | 10/2001 | Macevicz |
| 6,565,727 | B1 | 5/2003 | Shenderov et al. |
| 6,773,566 | B2 | 8/2004 | Shenderov et al. |
| 6,911,132 | B2 | 6/2005 | Pamula et al. |
| 6,969,488 | B2 | 11/2005 | Bridgham et al. |
| 6,977,033 | B2 | 12/2005 | Becker et al. |
| 7,001,792 | B2 | 2/2006 | Sauer et al. |
| 7,052,244 | B2 | 5/2006 | Fouillet et al. |
| 7,057,026 | B2 | 6/2006 | Barnes et al. |
| 7,163,612 | B2 | 1/2007 | Sterling et al. |
| 7,211,414 | B2 | 5/2007 | Hardin et al. |
| 7,315,019 | B2 | 1/2008 | Turner et al. |
| 7,328,979 | B2 | 2/2008 | Decre et al. |
| 7,329,492 | B2 | 2/2008 | Hardin et al. |
| 7,405,281 | B2 | 7/2008 | Xu et al. |
| 7,427,673 | B2 | 9/2008 | Balasubramanian et al. |
| 7,439,014 | B2 | 10/2008 | Pamula et al. |
| 7,541,444 | B2 | 6/2009 | Milton et al. |
| 7,547,360 | B2 | 6/2009 | Velev |
| 7,566,537 | B2 | 7/2009 | Balasubramanian et al. |
| 7,641,779 | B2 | 1/2010 | Becker et al. |
| 7,727,466 | B2 | 6/2010 | Meathrel et al. |
| 7,948,015 | B2 | 5/2011 | Rothberg |
| 7,985,565 | B2 | 7/2011 | Mayer et al. |
| 8,039,817 | B2 | 10/2011 | Feng et al. |
| 8,053,192 | B2 | 11/2011 | Bignell et al. |
| 8,182,989 | B2 | 5/2012 | Bignell et al. |
| 8,241,573 | B2 | 8/2012 | Banerjee et al. |
| 8,262,900 | B2 | 9/2012 | Rothberg et al. |
| 8,343,746 | B2 | 1/2013 | Rank |
| 8,349,167 | B2 | 1/2013 | Rothberg et al. |

(Continued)

FOREIGN PATENT DOCUMENTS

| WO | 1991/06678 A1 | 5/1991 |
| WO | 2002/080822 | 10/2002 |

(Continued)

OTHER PUBLICATIONS

Bentley, et al., "Accurate whole human genome sequencing using reversibe terminator chemistry", Nature, vol. 456, Nov. 6, 2006, 53-59.

Cockroft, et al., "A single-molecule nanpore device detects DNA polymerase activity with single-nucleotide resolution", J. Am. Chem. Soc, 130(3), Jan. 23, 2008, 818-820.

Deamer, et al., "Characterization of nucleic acids by nanopore analysis", ACC Chem Res, 35(10), 2002, 817-825.

Deamer, et al., "Nanopores and nucleic acids: prospects for ultrarapid sequencing", Trends Biotechnol, 18(4), 2000, 147-151.

Dhindsa, et al., "Virtual Electrowetting Channels: Electronic Liquid Transport with Continuous Channel Functionality", Lab on a Chip, vol. 10, 2010, 832-836.

(Continued)

*Primary Examiner* — Eric S Dejong
(74) *Attorney, Agent, or Firm* — Illumina, Inc.

(57) ABSTRACT

Method includes providing a droplet actuator having a droplet-operations gap and a plurality of electrodes positioned along the droplet-operations gap. The method also includes positioning an input droplet in the droplet-operations gap. The input droplet has a starting concentration of a substance-of-interest. The method also includes conducting droplet operations within the droplet-operations gap using the electrodes to generate discrete dilution droplets that are formed from the input droplet. The dilution droplets and a remainder of the input droplet form a droplet set. At least two of the dilution droplets in the droplet set having different concentrations of the substance-of-interest. The method also includes combining a select number of the droplets from the droplet set to form an output droplet having a modified concentration that is substantially equal to a designated target concentration.

20 Claims, 12 Drawing Sheets

(56) References Cited

U.S. PATENT DOCUMENTS

| | | | |
|---|---|---|---|
| 8,460,910 | B2 | 6/2013 | Smith et al. |
| 8,623,628 | B2 | 1/2014 | Ost et al. |
| 8,865,410 | B2 | 10/2014 | Shendure et al. |
| 9,675,972 | B2 | 6/2017 | Pollack et al. |
| 2010/0236929 | A1* | 9/2010 | Pollack ............... B01L 3/50273 204/450 |

FOREIGN PATENT DOCUMENTS

| | | |
|---|---|---|
| WO | 2004/018497 A2 | 3/2004 |
| WO | 2005/065814 A1 | 7/2005 |
| WO | 2006/064199 | 6/2006 |
| WO | 2007/010251 | 1/2007 |
| WO | 2007/120241 | 10/2007 |
| WO | 2007/123744 A2 | 11/2007 |
| WO | 2008/042067 | 4/2008 |
| WO | 2008/098236 | 8/2008 |
| WO | 2008/101194 | 8/2008 |
| WO | 2008/116221 | 9/2008 |
| WO | 2008/134153 | 11/2008 |
| WO | 2009/021173 | 2/2009 |
| WO | 2010/027894 | 3/2010 |
| WO | 2013/117595 | 8/2013 |
| WO | 2013/131962 | 9/2013 |

OTHER PUBLICATIONS

Healy, K., "Nanopore-based single-molecule DNA analysis", Nanomed. 2(4), 2007, 459-481.

Korlach, et al., "Selective aluminum passivation for targeted immobilization of single DNA polyrnerase molecules in zero-mode waveguide nanostructures", PNAS, vol. 105 No. 4, 2008, 1176-1181.

Levene, et al., "Zero-Mode Waveguides for Single-Molecule Analysis at high concentrations", Science 299, 2003, 682-686.

Li , et al., "DNA molecules and configurations in a solid-state nanopore microscope", Nature Mater, 2(9), 2003, 611-615.

Lundquist, et al., "Parallel confocal detection of single molecules in real time", Opt. Lett 33(9), 2008, 1026-1028.

Metzker, et al., "Emerging technologies in DNA sequencing", Genome Research, 15, 2005, 1767-1776.

Ronaghi, M, et al., "A Sequencing Method Based on Real-Time Phyrophosphate", Science 281 (5375), Jul. 17, 1998; 363-365.

Ronaghi, M., "Pyrosequencing sheds light on DNA sequencing", Genome Res, 11(1), 2001, 3-11.

Ronaghi, M., et al., "Real-time DNA sequencing using detection of pyrophosphate release", Anal. Biochem. Nov. 1, 1996; 242 (1):84-9, Nov. 1, 1996, 84-89.

Ruparel, et al., "Design and synthesis of a 3'-O-allyl photocleavable fluorescent nucleotide as a reversible terminator for DNA sequencing by synthesis", PNAS, 102, 2005, 5932-5937.

Soni, et al., "Progress toward Ultrafast DNA Sequencing Using Solid-State Nanopores", Clin Chem, 53(11), 2007, 1996-2001.

* cited by examiner

| NAME | INDEX 1 – INDEX 2 | QUANT | NORM | COMMENTS |
|---|---|---|---|---|
| Sample01 | NR006 – GCCAAT | 6.11 | 5.38 | Normalized value is <8nM. Qualify library manually to determine usability |
| Sample_02 | NR013 – AGTCAA | 16.20 | 10.05 | Ready |
| Sample_03 | NR012 – CTTGTA | 19.98 | 10.13 | Ready |
| Sample_04 | NR014 – AGTTCC | 25.40 | 9.99 | Ready |
| Sample_05 | NR005 – ACAGTG | 18.50 | 9.83 | Ready |
| Sample_06 | NR015 – ATGTCA | 21.22 | 9.34 | Ready |
| Sample_07 | NR019 – GTGAAA | 59.96 | 9.98 | Ready |
| Sample_08 | NR021 – GTTTCG | 46.26 | 9.84 | Ready |
| Sample_09 | NR001 – ATCACG | 43.59 | 9.59 | Ready |
| Sample_10 | NR010 – TAGCTT | 61.57 | 9.78 | Ready |
| Sample_11 | NR020 – GTGGCC | Too High to Quant | Unable to Norm | Sample concentration exceeds linear curve range. Qualify library manually. |
| Sample_12 | NR008 – ACTTGA | 28.50 | 9.61 | Ready |
| Sample_13 | NR025 – ACTGAT | 61.67 | 9.80 | Ready |
| Sample_14 | NR011 – GGCTAC | 34.90 | 9.98 | Ready |
| Sample_15 | NR018 – GTCCGC | 1.57 | 1.38 | Normalized value is <8nM. Qualify library manually to determine usability |
| Sample_16 | NR023 – GAGTGG | 41.21 | 10.62 | Ready |

FIG. 10

[Standard Information]

| ID | Side | Known ng/uL Concentration | Measured Fluorescence |
|---|---|---|---|
| 0 | L | 0.00 | 1359.95 |
| 1 | L | 3.13 | 25548.37 |
| 2 | L | 6.25 | 50755.29 |
| 3 | L | 12.50 | 106740.83 |
| 4 | L | 25.00 | 202565.52 |
| 5 | L | 50.00 | 417041.84 |
| 0 | R | 0.00 | 1762.83 |
| 1 | R | 3.13 | 26759.52 |
| 2 | R | 6.25 | 54378.08 |
| 3 | R | 12.50 | 108226.65 |
| 4 | R | 25.00 | 223021.98 |
| 5 | R | 50.00 | 444570.46 |

[Standard Curves]

| Side | Slope | Intercept | $R^2$ | Outlier |
|---|---|---|---|---|
| L | 8304.93768818008 | −88.17341409382 | 0.999666170173633 | |
| R | 8899.25837332465 | −566.020994285849 | 0.999904459564279 | |

FIG. 11

| COMMENT | MEANING | ADVISED ACTION |
|---|---|---|
| Ready | Library preparation, quantification, and normalization proceeded normally. | Collect libraries, separate from oil, and proceed with sequencing |
| Optical calibration did not pass QC metrics for this lane. Quantify library manually | The indicated libraries could not be quantified because optical calibration on that side of the library card did not meet QC requirements to be used to quantify libraries accurately. This can be due to reagent loading error, reagent evaporation, or general fluidic/dispense issues | Quantify collected library manually using optional methods as described in assay-specific user guide. May need to dilute library before sequencing |
| Standard curve did not meet QC metrics for this lane. Quantify library manually | The standard curve for that side of the library card required removing more than one standard to meet QC requirements to be used to quantify libraries accurately. This can be due to loading error, reagent evaporation, or general fluidic/dispense issues | Quantify collected library manually using optional methods as described in assay-specific user guide. May need to dilute library before sequencing |
| Sample concentration exceeds linear curve range. Quantify library manually | Sample concentration exceeds highest standard, unable to quantify. Libraries are moved to the collection wells without normalization and quantification values from NeoPrep are not able to be provided | Quantify collected library manually using optional methods as described in assay-specific user guide. May need to dilute library before sequencing |
| Quantified value is <8 nM. Qualify library manually to determine usability | Sample concentration is less than optimal but may still perform well in sequencing, depending on application requirement | Qualify collected library to determine usability |
| Quantified value is <3 nM. Qualify library manually to determine usability, as library with very low yield may not perform well in sequencing | Sample concentration is very low. Sample may not constitute complete library | Qualify collected library to determine usability. May need to repeat library prep |
| Normalized value is <8 nM. Qualify library manually to determine usability | Sample concentration is less than optimal but may still perform well in sequencing, depending on application requirement | Qualify collected library to determine usability |
| Normalized value is >12 nM. Qualify library manually to determine usability | Sample concentration is unusually high, may be an error in Quant/Norm | Qualify collected library to determine usability. May need to dilute before sequencing |

SYSTEMS AND METHODS FOR OBTAINING A DROPLET HAVING A DESIGNATED CONCENTRATION OF A SUBSTANCE-OF-INTEREST

CROSS-REFERENCE TO RELATED APPLICATIONS

The present application claims the benefit of U.S. Provisional Application No. 62/217,199, filed on Sep. 11, 2015, and U.S. Provisional Application No. 62/253,488, filed on Nov. 10, 2015, each of which is incorporated herein by reference in its entirety.

BACKGROUND

A droplet actuator typically includes one or more substrates configured to form a surface or gap for conducting droplet operations. The one or more substrates establish a droplet operations surface or gap for conducting droplet operations and may also include electrodes arranged to conduct the droplet operations. The droplet operations substrate or the gap between the substrates may be coated or filled with a filler fluid that is immiscible with the liquid that forms the droplets. Droplets that are processed in a droplet actuator can have any concentration of a substance-of-interest, such as genetic material. This can be problematic, especially when mixing and/or processing droplets of different concentrations. Therefore, new approaches are needed for managing the concentration of droplets on a droplet actuator.

BRIEF DESCRIPTION

In an embodiment, a method is provided that includes providing a droplet actuator having a droplet-operations gap and a plurality of electrodes positioned along the droplet-operations gap. The method also includes positioning an input droplet in the droplet-operations gap. The input droplet has a starting concentration of a substance-of-interest. The method also includes conducting droplet operations within the droplet-operations gap using the electrodes to generate discrete dilution droplets that are formed from the input droplet. The dilution droplets form a droplet set. Optionally, a remainder of the input droplet also forms a part of the droplet set. At least two of the dilution droplets in the droplet set having different concentrations of the substance-of-interest. The method also includes combining a select number of the droplets from the droplet set to form an output droplet having a modified concentration that is substantially equal to a designated target concentration.

In an embodiment, a method is provided that includes providing a droplet actuator having a droplet-operations gap and a plurality of electrodes positioned along the droplet-operations gap. The method also includes positioning first and second input droplets within the droplet-operations gap. The first input droplet has a first concentration of a first sample. The second input droplet has a second concentration of a second sample. The method also includes conducting droplet operations within the droplet-operations gap using the electrodes to generate discrete dilution droplets that are formed from the first input droplet. The dilution droplets form a droplet set. Optionally, a remainder of the first input droplet also forms a part of the droplet set. At least two of the dilution droplets in the droplet set have different concentrations of the substance-of-interest. The method also includes combining a select number of the droplets from the droplet set to form an output droplet. The output droplet has a modified concentration of the first sample that is substantially equal to the second concentration of the second sample.

In an embodiment, a system is provided that includes a droplet actuator having a droplet-operations gap and a plurality of electrodes positioned along the droplet-operations gap. The droplet-operations gap is configured to receive an input droplet. The input droplet has a starting concentration of a substance-of-interest. The system also includes a controller that is operably coupled to the electrodes of the droplet actuator. The controller is configured to control the electrodes to conduct droplet operations within the droplet-operations gap using the electrodes to generate discrete dilution droplets that are formed from the input droplet. The dilution droplets form a droplet set. Optionally, a remainder of the input droplet also forms a part of the droplet set. At least two of the dilution droplets in the droplet set have different concentrations of the substance-of-interest. The controller is configured to control the electrodes to combine a select number of the droplets from the droplet set to form an output droplet. The output droplet has a modified concentration of the substance-of-interest that is substantially equal to a designated target concentration.

In an embodiment, a system is provided that includes a droplet actuator having a droplet-operations gap and a plurality of electrodes positioned along the droplet-operations gap. The droplet-operations gap is configured to receive an input droplet. The input droplet has a starting concentration of a substance-of-interest. The system also includes a controller that is operably coupled to the electrodes of the droplet actuator. The controller is configured to control the electrodes to conduct droplet operations within the droplet-operations gap using the electrodes to generate discrete dilution droplets that are formed from the first input droplet. The dilution droplets form a droplet set. Optionally, a remainder of the first input droplet also forms a part of the droplet set. At least two of the dilution droplets in the droplet set having different concentrations of the substance-of-interest. The controller is configured to control the electrodes to combine a select number of the droplets from the droplet set to form an output droplet. The output droplet has a modified concentration of the first sample that is substantially equal to the second concentration of the second sample.

In an embodiment, a method is provided that includes loading sample droplets into a droplet actuator. The droplet actuator has a droplet-operations gap and a plurality of electrodes positioned along the droplet-operations gap. The sample droplets are separated from one another in the droplet-operations gap and include a substance-of-interest. The method also includes determining respective concentrations of the substance-of-interest in the sample droplets. The method also includes adjusting the respective concentration of at least one of the sample droplets so that each of the respective concentrations of at least a plurality of the sample droplets is substantially equal to a target concentration. Adjusting the respective concentration of a corresponding sample droplet includes conducting droplet operations within the droplet-operations gap using the electrodes to generate discrete dilution droplets that are formed from a corresponding sample droplet. The dilution droplets form a droplet set. Optionally, a remainder of the sample droplet also forms a part of the droplet set. At least two of the dilution droplets in the droplet set have different concentrations of the substance-of-interest. Adjusting the respective concentration of a corresponding sample droplet also includes combining a select number of the droplets from the droplet set to form an output droplet having a modified concentration. The select number of the droplets is based on the respective concentration of the corresponding sample droplet and the target concentration.

In an embodiment, a system is provided that includes a droplet actuator having a droplet-operations gap and a plurality of electrodes positioned along the droplet-operations gap. The droplet actuator is configured to receive discrete sample droplets in the droplet-operations gap. The system also includes a controller that is operably coupled to the electrodes of the droplet actuator. The controller is configured to control the electrodes to determine respective concentrations of a substance-of-interest in the sample droplets and adjust the respective concentration of at least one of the sample droplets so that each of the respective concentrations of at least a plurality of the sample droplets is substantially equal to a target concentration. Adjusting the respective concentration of a corresponding sample droplet includes conducting droplet operations within the droplet-operations gap using the electrodes to generate discrete dilution droplets that are formed from the corresponding sample droplet. The dilution droplets form a droplet set. Optionally, a remainder of the sample droplet also forms a part of the droplet set. At least two of the dilution droplets in the droplet set have different concentrations of the substance-of-interest. Adjusting the respective concentration of a corresponding sample droplet also includes combining a select number of the droplets from the droplet set to form an output droplet. The select number of the droplets is based on the concentration of the corresponding sample droplet and the target concentration.

In particular embodiments, the droplet set includes a remainder (if any) of the sample droplet. In other embodiments, the droplet set does not include the remainder (if any) of the sample droplet.

BRIEF DESCRIPTION OF THE DRAWINGS

FIG. 10 shows a first portion of a library report generated by the system of FIG. 7.

FIG. 11 shows a second portion of the library report of FIG. 10 generated by the system of FIG. 7.

FIG. 12 includes a table that describes how to interpret comments in the library report of FIGS. 10 and 11 and what, if any, actions should be taken.

DETAILED DESCRIPTION

Figure 1:
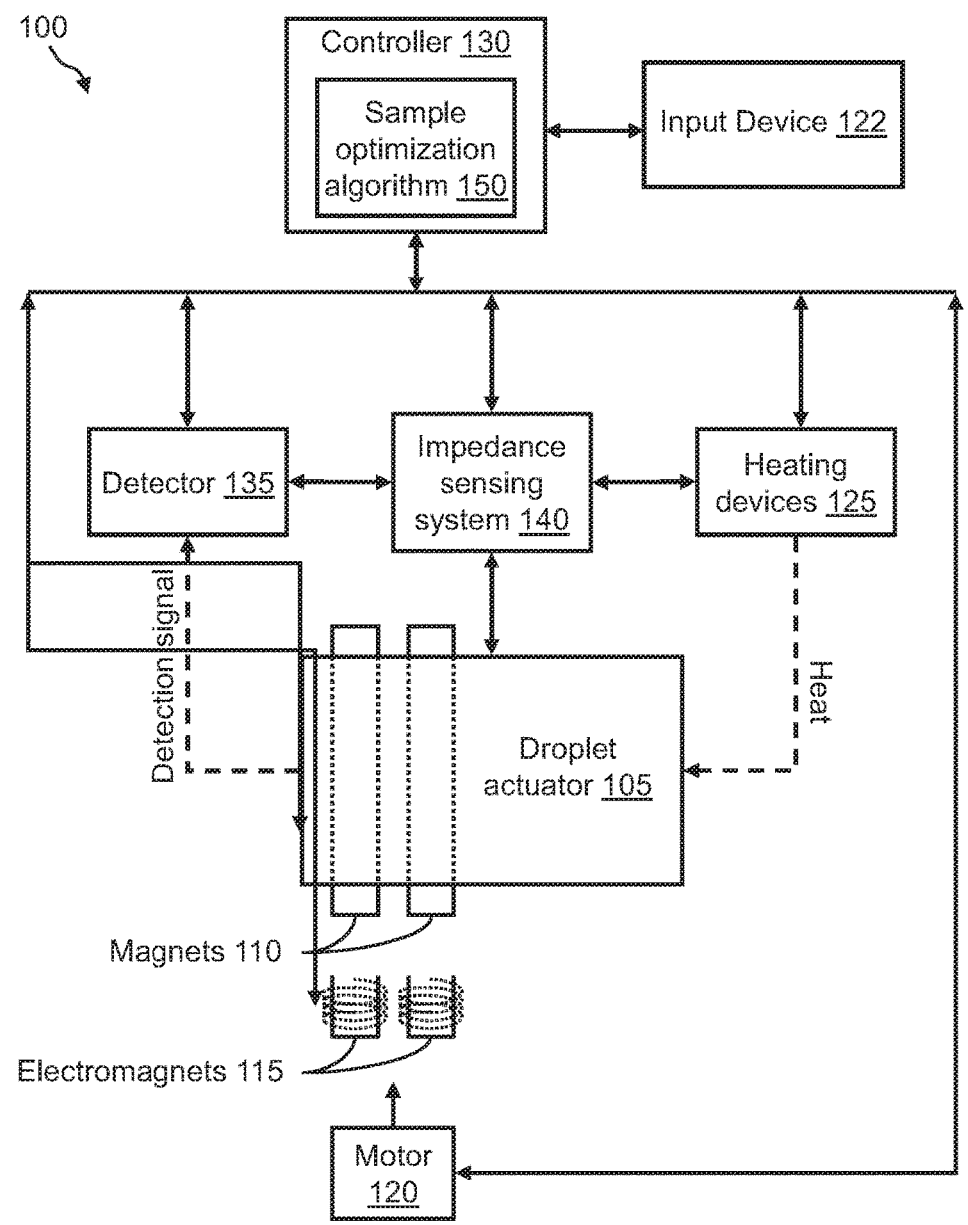
FIG. 1 illustrates a functional block diagram of an example of a microfluidics system for performing a concentration-adjustment process on a droplet actuator.

The methods and systems described herein can be used in conjunction with a variety of biological or chemical analysis techniques, including nucleic acid sequencing techniques. Embodiments may include a droplet actuator having a droplet-operations gap and a plurality of electrodes positioned along the droplet-operations gap. Embodiments are configured to receive an input droplet having a known or unknown concentration of a substance-of-interest. The input droplet may also be referred to as a "sample droplet" in some embodiments. The substance-of-interest may be, for example, nucleic acids. In particular embodiments, the nucleic acids are from an individual source (e.g., human, animal, plant, bacteria, virus, or anything having DNA or RNA), although the droplet may have nucleic acids from multiple sources. Embodiments are configured to conduct droplet operations to modify the concentration of the input droplet such that the input droplet has a designated concentration, which may be referred to as the modified concentration. The input droplet is typically diluted so that the modified concentration is less than the starting concentration. In other embodiments, however, the starting concentration may be less than the modified concentration.

The modified concentration may be substantially equal to a target concentration. For example, a modified concentration may be substantially equal to a target concentration if the modified concentration is within 40% of the target concentration. For example, if the target concentration is 100 nM, then the modified concentration must be 70 nM or 130 nM. In other words, the modified concentration must be between 70% and 130% of the target concentration. In certain embodiments, a modified concentration may be substantially equal to a target concentration if the modified concentration is within 30% or 20% of the target concentration or within 15% of the target concentration. In particular embodiments, a modified concentration may be substantially equal to a target concentration if the modified concentration is within 15% of the target concentration, within 10% of the target concentration, or within 5% of the target concentration. Yet in more particular embodiments, a modified concentration may be substantially equal to a target concentration if the modified concentration is within 3% of the target concentration, within 2% of the target concentration, or within 1% of the target concentration.

By modifying the concentration of one or more droplets so that two or more droplets have substantially equal concentrations (e.g., normalizing the concentrations), a variety of protocols may be performed. For embodiments that include SBS sequencing, sample droplets can be provided that each contain genetic material from a single source (e.g. a single individual such as a human or single tissue from an individual such as a tissue suspected of being diseased). The genetic material in each droplet can be attached to synthetic tags such as nucleic acid adapters having one or more tag sequences that are associated with the respective source. The droplets can be processed using methods set forth herein such that they have substantially equal concentrations of genetic material and they may be combined to form a sample pool so that SBS sequencing may be simultaneously conducted for each of the samples. Because genetic material has been tagged to indicate its source, and sequencing can be carried out to decipher the tag and the genetic material to which it is attached, target sequences obtained from the mixture can be correlated to their respective sources. Sequences of the different samples may then be identified through subsequent analysis. Such protocols are described in greater detail in U.S. Pat. Nos. 8,053,192, 8,182,989, and 8,865,410; and U.S. Patent Application Publication No. 2014/0364323, each of which is incorporated herein by reference in its entirety. Other protocols exist in which it may be desirable to have two different solutions with substantially equal concentrations of a substance so that, for example, any data received analyzing the substances may be compared.

As used herein, the term "substance-of-interest" includes any biological, biochemical, and/or chemical substance that is capable of being disposed in a droplet of a solution, wherein the droplet is capable of being manipulated through electrowetting-mediated droplet operations. The substance-of-interest may include a variety of biological/biochemical/chemical substances that are suitable for being observed (e.g., imaged) or examined. For example, biological/biochemical/chemical substances may include biomolecules, nucleosides, nucleic acids, polynucleotides, oligonucleotides, proteins, enzymes, polypeptides, antibodies, antigens, ligands, receptors, polysaccharides, carbohydrates, polyphosphates, nanopores, organelles, lipid layers, cells, cell lysates, tissues, organs, organisms, bodily fluids. A substance-of-interest may include biologically active chemical compound(s), such as analogs or mimetics of aforementioned species. A substance-of-interest may include biological samples such as cell lysates, intact cells, organisms, organs, tissues and bodily fluids. "Bodily fluids" may include, but are not limited to, blood, dried blood, clotted blood, serum, plasma, saliva, cerebral spinal fluid, pleural fluid, tears, lactal duct fluid, lymph, sputum, urine, amniotic fluid, and semen. A sample may include a bodily fluid that is "acellular." An "acellular bodily fluid" includes less than about 1% (w/w) whole cellular material. Plasma or serum are examples of acellular bodily fluids. A sample may include a specimen of natural or synthetic origin (i.e., a cellular sample made to be acellular). In some embodiments, the biological sample can be from a human or from a non-human origin. In some embodiments, the biological sample can be from a human patient. In some embodiments, the biological sample can be from a newborn human.

Embodiments may be particularly suitable in library preparation for sequencing-by-synthesis (SBS) techniques. SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery.

In one exemplary type of SBS, cycle sequencing is accomplished by stepwise addition of reversible terminator nucleotides containing, for example, a cleavable or photobleachable dye label as described, for example, in International Patent Pub. No. WO 04/018497 and U.S. Pat. No. 7,057,026, the disclosures of which are incorporated herein by reference. This approach is being commercialized by Solexa (now Illumina Inc.), and is also described in International Patent Pub. No. WO 91/06678 and International Patent Pub. No. WO 07/123,744, each of which is incorporated herein by reference. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

Preferably in reversible terminator-based sequencing embodiments, the labels do not substantially inhibit extension under SBS reaction conditions. However, the detection labels can be removable, for example, by cleavage or degradation. Images can be captured following incorporation of labels into arrayed nucleic acid features. In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially and an image of the array can be obtained between each addition step. In such embodiments each image will show nucleic acid features that have incorporated nucleotides of a particular type. Different features will be present or absent in the different images due the different sequence content of each feature. However, the relative position of the features will remain unchanged in the images. Images obtained from such reversible terminator-SBS methods can be stored, processed and analyzed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth below.

In particular embodiments some or all of the nucleotide monomers can include reversible terminators. In such embodiments, reversible terminators/cleavable fluors can include fluor linked to the ribose moiety via a 3' ester linkage (Metzker, Genome Res. 15:1767-1776 (2005), which is incorporated herein by reference). Other approaches have separated the terminator chemistry from the cleavage of the fluorescence label (Ruparel et al., Proc Natl Acad Sci USA 102: 5932-7 (2005), which is incorporated herein by reference in its entirety). Ruparel et al described the development of reversible terminators that used a small 3' allyl group to block extension, but could be deblocked by a short treatment with a palladium catalyst. The fluorophore was attached to the base via a photocleavable linker that could be cleaved by a 30 second exposure to long wavelength UV light. Either disulfide reduction or photocleavage can be used to cleave linkers, for example. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination. Examples of modified nucleotides are also described in U.S. Pat. Nos. 7,427,673, and 7,057,026, the disclosures of which are incorporated herein by reference in their entireties.

Additional exemplary SBS systems and methods which can be utilized with the methods and systems described herein are described in U.S. Pat. Nos. 7,541,444, 7,566,537, 7,057,026, 8,460,910, 8,623,628, International Patent Pub. No. WO 05/065814, U.S. Pat. No. 7,985,565, International Patent Pub. No. WO 06/064199, International Patent Pub. No. WO 07/010,251, U.S. Patent Pub. No. 20120270305 and U.S. Patent Pub. No. 20130260372, the disclosures of which are incorporated herein by reference in their entireties.

Some embodiments can utilize detection of four different nucleotides using fewer than four different labels. For example, SBS can be performed utilizing methods and systems described in the incorporated materials of U.S. Patent Pub. No. 20130079232. As a first example, a pair of nucleotide types can be detected at the same wavelength, but distinguished based on a difference in intensity for one member of the pair compared to the other, or based on a change to one member of the pair (e.g., via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc.). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples is a fluorescence-based SBS method that uses a first nucleotide type that is detected in a first channel (e.g., dATP having a label that is detected in the first channel when excited by a first excitation wavelength), a second nucleotide type that is detected in a second channel (e.g., dCTP having a label that is detected in the second channel when excited by a second excitation wavelength), a third nucleotide type that is detected in both the first and the second channel (e.g., dTTP having at least one label that is detected in both channels when excited by the first and/or second excitation wavelength) and a fourth nucleotide type that lacks a label that is not, or minimally, detected in either channel (e.g., dGTP having no label).

Further, as described in the incorporated materials of U.S. Patent Pub. No. 20130079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can utilize sequencing by ligation techniques. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features will be present or absent in the different images due to the different sequence content of each feature, but the relative position of the features will remain unchanged in the images. Images obtained from ligation-based sequencing methods can be stored, processed and analyzed as set forth herein. Exemplary SBS systems and methods which can be utilized with the methods and systems described herein are described in U.S. Pat. Nos. 6,969,488, 6,172,218, and 6,306,597, the disclosures of which are incorporated herein by reference in their entireties.

Some embodiments may utilize pyrosequencing. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons. The nucleic acids to be sequenced can be attached to features in an array and the array can be imaged to capture the chemiluminescent signals that are produced due to incorporation of nucleotides at the features of the array. An image can be obtained after the array is treated with a particular nucleotide type (e.g., A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

Some embodiments can utilize nanopore sequencing (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis". Acc. Chem. Res. 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003), the disclosures of which are incorporated herein by reference in their entireties). In such embodiments, the target nucleic acid passes through a nanopore, although some nanopore embodiments can utilize methods involving the real-time monitoring of DNA polymerase nucleotide incorporation. The nanopore can be a synthetic pore or biological membrane protein, such as α-hemolysin. In one exemplary embodiment, as the target nucleic acid passes through the nanopore, each base can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nucleotide resolution." J. Am. Chem. Soc. 130, 818-820 (2008), the disclosures of which are incorporated herein by reference in their entireties). Data obtained from nanopore sequencing can be stored, processed and analyzed as set forth herein. In particular, the data can be treated as an image in accordance with the exemplary treatment of optical images and other images that is set forth herein.

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414 (each of which is incorporated herein by reference) or nucleotide incorporations can be detected with zero-mode waveguides as described, for example, in U.S. Pat. No. 7,315,019 (which is incorporated herein by reference) and using fluorescent nucleotide analogs and engineered polymerases as described, for example, in U.S. Pat. Nos. 7,405,281 and 8,343,746 (each of which is incorporated herein by reference). The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nano structures." Proc. Natl. Acad. Sci. USA 105, 1176-1181 (2008), the disclosures of which are incorporated herein by reference in their entireties). Images obtained from such methods can be stored, processed and analyzed as set forth herein.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in U.S. Pat. Nos. 8,262,900; 7,948,015; U.S. Patent Pub. No. 20100137143; or U.S. Pat. No. 8,349,167, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

The above SBS methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion polymerase chain reaction (PCR) as described in further detail below.

The methods set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

An advantage of the methods set forth herein is that they provide for rapid and efficient detection of a plurality of target nucleic acids in parallel. Accordingly the present disclosure provides integrated systems capable of preparing and detecting nucleic acids using techniques known in the art such as those exemplified above. Thus, an integrated system of the present disclosure can include fluidic components capable of delivering amplification reagents and/or sequencing reagents to one or more immobilized DNA fragments, the system comprising components such as pumps, valves, reservoirs, fluidic lines and the like. A flow cell can be configured and/or used in an integrated system for detection of target nucleic acids. Exemplary flow cells are described, for example, in U.S. Pat. No. 8,241,573 and U.S. Patent Pub. No. 20120270305, each of which is incorporated herein by reference. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeq™ platform (Illumina, Inc., San Diego, Calif.) and devices described in U.S. Patent Pub. No. 20120270305, which is incorporated herein by reference.

As used herein, "activate," with reference to one or more electrodes, means affecting a change in the electrical state of the one or more electrodes which, in the presence of a droplet, results in a droplet operation. Activation of an electrode can be accomplished using alternating current (AC) or direct current (DC). Any suitable voltage may be used. For example, an electrode may be activated using a voltage which is greater than about 150 V, or greater than about 200 V, or greater than about 250 V, or from about 275 V to about 1000 V, or about 300 V. Where an AC signal is used, any suitable frequency may be employed. For example, an electrode may be activated using an AC signal having a frequency from about 1 Hz to about 10 MHz, or from about 10 Hz to about 60 Hz, or from about 20 Hz to about 40 Hz, or about 30 Hz.

"Bead," with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical, amorphous and other three dimensional shapes. The bead may, for example, be capable of being subjected to a droplet operation in a droplet on a droplet actuator or otherwise configured with respect to a droplet actuator in a manner which permits a droplet on the droplet actuator to be brought into contact with the bead on the droplet actuator and/or off the droplet actuator. Beads may be provided in a droplet, in a droplet operations gap, or on a droplet operations surface. Beads may be provided in a reservoir that is external to a droplet operations gap or situated apart from a droplet operations surface, and the reservoir may be associated with a flow path that permits a droplet including the beads to be brought into a droplet operations gap or into contact with a droplet operations surface. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead, a portion of a bead, or only one component of a bead. The remainder of the bead may include, among other things, polymeric material, coatings, and moieties which permit attachment of an assay reagent. Examples of suitable beads include flow cytometry microbeads, polystyrene microparticles and nanoparticles, functionalized polystyrene microparticles and nanoparticles, coated polystyrene microparticles and nanoparticles, silica microbeads, fluorescent microspheres and nanospheres, functionalized fluorescent microspheres and nanospheres, coated fluorescent microspheres and nanospheres, color dyed microparticles and nanoparticles, magnetic microparticles and nanoparticles, superparamagnetic microparticles and nanoparticles (e.g., DYNABEADS® particles, available from Invitrogen Group, Carlsbad, Calif.), fluorescent microparticles and nanoparticles, coated magnetic microparticles and nanoparticles, ferromagnetic microparticles and nanoparticles, coated ferromagnetic microparticles and nanoparticles, and those described in Watkins et al., U.S. Patent Pub. No. 20050260686, entitled "Multiplex Flow Assays Preferably with Magnetic Particles as Solid Phase," published on Nov. 24, 2005; Chandler., U.S. Patent Pub. No. 20030132538, entitled "Encapsulation of Discrete Quanta of Fluorescent Particles," published on Jul. 17, 2003; Chandler et al., U.S. Patent Pub. No. 20050118574, entitled "Multiplexed Analysis of Clinical Specimens Apparatus and Method," published on Jun. 2, 2005; Chandler et al., U.S. Patent Pub. No. 20050277197, entitled "Microparticles with Multiple Fluorescent Signals and Methods of Using Same," published on Dec. 15, 2005; and Chandler et al., U.S. Patent Pub. No. 20060159962, entitled "Magnetic Microspheres for use in Fluorescence-based Applications," published on Jul. 20, 2006, the entire disclosures of which are incorporated herein by reference for their teaching concerning beads and magnetically responsive materials and beads. Beads may be pre-coupled with a biomolecule or other substance that is able to bind to and form a complex with a biomolecule. Beads may be pre-coupled with an antibody, protein or antigen, DNA/RNA probe or any other molecule with an affinity for a desired target. Examples of droplet actuator techniques for immobilizing magnetically responsive beads and/or non-magnetically responsive beads and/or conducting droplet operations protocols using beads are described in Pollack et al., U.S. Patent Pub. No. 20080053205, entitled "Droplet-Based Particle Sorting," published on Mar. 6, 2008; U.S. Patent App. No. 61/039,183, entitled "Multiplexing Bead Detection in a Single Droplet," filed on Mar. 25, 2008; Pamula et al., U.S. Patent App. No. 61/047,789, entitled "Droplet Actuator Devices and Droplet Operations Using Beads," filed on Apr. 25, 2008; U.S. Patent App. No. 61/086,183, entitled "Droplet Actuator Devices and Methods for Manipulating Beads," filed on Aug. 5, 2008; Eckhardt et al., International Patent Pub. No. WO/2008/098236, entitled "Droplet Actuator Devices and Methods Employing Magnetic Beads," published on Aug. 14, 2008; Grichko et al., International Patent Pub. No. WO/2008/134153, entitled "Bead-based Multiplexed Analytical Methods and Instrumentation," published on Nov. 6, 2008; Eckhardt et al., International Patent Pub. No. WO/2008/116221, "Bead Sorting on a Droplet Actuator," published on Sep. 25, 2008; and Eckhardt et al., International Patent Pub. No. WO/2007/120241, entitled "Droplet-based Biochemistry," published on Oct. 25, 2007, the entire disclosures of which are incorporated herein by reference. Bead characteristics may be employed in the multiplexing aspects of the present disclosure. Examples of beads having characteristics suitable for multiplexing, as well as methods of detecting and analyzing signals emitted from such beads, may be found in Whitman et al., U.S. Patent Pub. No. 20080305481, entitled "Systems and Methods for Multiplex Analysis of PCR in Real Time," published on Dec. 11, 2008; Roth, U.S. Patent Pub. No. 20080151240, "Methods and Systems for Dynamic Range Expansion," published on Jun. 26, 2008; Sorensen et al., U.S. Patent Pub. No. 20070207513, entitled "Methods, Products, and Kits for Identifying an Analyte in a Sample," published on Sep. 6, 2007; Roth, U.S. Patent Pub. No. 20070064990, entitled "Methods and Systems for Image Data Processing," published on Mar. 22, 2007; Chandler et al., U.S. Patent Pub. No. 20060159962, entitled "Magnetic Microspheres for use in Fluorescence-based Applications," published on Jul. 20, 2006; Chandler et al., U.S. Patent Pub. No. 20050277197, entitled "Microparticles with Multiple Fluorescent Signals and Methods of Using Same," published on Dec. 15, 2005; and Chandler et al., U.S. Patent Publication No. 20050118574, entitled "Multiplexed Analysis of Clinical Specimens Apparatus and Method," published on Jun. 2, 2005, the entire disclosures of which are incorporated herein by reference.

"Droplet" means a volume of liquid on a droplet actuator. Typically, a droplet is at least partially bounded by a filler fluid. For example, a droplet may be completely surrounded by a filler fluid or may be bounded by filler fluid and one or more surfaces of the droplet actuator. As another example, a droplet may be bounded by filler fluid, one or more surfaces of the droplet actuator, and/or the atmosphere. As yet another example, a droplet may be bounded by filler fluid and the atmosphere. Droplets may, for example, be aqueous or non-aqueous or may be mixtures or emulsions including aqueous and non-aqueous components. A droplet may be completely or partially bounded by a gas such as atmosphere or inert gas such as argon or nitrogen. Droplets may take a wide variety of shapes; nonlimiting examples include generally disc shaped, slug shaped, truncated sphere, ellipsoid, spherical, partially compressed sphere, hemispherical, ovoid, cylindrical, combinations of such shapes, and various shapes formed during droplet operations, such as merging or splitting or formed as a result of contact of such shapes with one or more surfaces of a droplet actuator. For examples of droplet fluids that may be subjected to droplet operations using the approach of the present disclosure, see Eckhardt et al., International Patent Pub. No. WO/2007/120241, entitled, "Droplet-Based Biochemistry," published on Oct. 25, 2007, the entire disclosure of which is incorporated herein by reference.

In various embodiments, a droplet may include a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes. Moreover, a droplet may include a reagent, such as water, deionized water, saline solutions, acidic solutions, basic solutions, detergent solutions and/or buffers. A droplet can include nucleic acids, such as DNA, genomic DNA, RNA, mRNA or analogs thereof; nucleotides such as deoxyribonucleotides, ribonucleotides or analogs thereof such as analogs having terminator moieties such as those described in Bentley et al., Nature 456:53-59 (2008); Gormley et al., International Patent Pub. No. WO/2013/131962, entitled, "Improved Methods of Nucleic Acid Sequencing," published on Sep. 12, 2013; Barnes et al., U.S. Pat. No. 7,057,026, entitled "Labelled Nucleotides," issued on Jun. 6, 2006; Kozlov et al., International Patent Pub. No. WO/2008/042067, entitled, "Compositions and Methods for Nucleotide Sequencing," published on Apr. 10, 2008; Rigatti et al., International Patent Pub. No. WO/2013/117595, entitled, "Targeted Enrichment and Amplification of Nucleic Acids on a Support," published on Aug. 15, 2013; Hardin et al., U.S. Pat. No. 7,329,492, entitled "Methods for Real-Time Single Molecule Sequence Fetermination," issued on Feb. 12, 2008; Hardin et al., U.S. Pat. No. 7,211,414, entitled "Enzymatic Nucleic Acid Synthesis: Compositions and Methods for Altering Monomer Incorporation Fidelity," issued on May 1, 2007; Turner et al., U.S. Pat. No. 7,315,019, entitled "Arrays of Optical Confinements and Uses Thereof," issued on Jan. 1, 2008; Xu et al., U.S. Pat. No. 7,405,281, entitled "Fluorescent Nucleotide Analogs and Uses Therefor," issued on Jul. 29, 2008; and Rank et al., U.S. Patent Pub. No. 20080108082, entitled "Polymerase Enzymes and Reagents for Enhanced Nucleic Acid Sequencing," published on May 8, 2008, the entire disclosures of which are incorporated herein by reference; enzymes such as polymerases, ligases, recombinases, or transposases; binding partners such as antibodies, epitopes, streptavidin, avidin, biotin, lectins or carbohydrates; or other biochemically active molecules. Other examples of droplet contents include reagents, such as a reagent for a biochemical protocol, such as a nucleic acid amplification protocol, an affinity-based assay protocol, an enzymatic assay protocol, a sequencing protocol, and/or a protocol for analyses of biological fluids. A droplet may include one or more beads.

"Droplet Actuator" means a device for manipulating droplets. For examples of droplet actuators, see Pamula et al., U.S. Pat. No. 6,911,132, entitled "Apparatus for Manipulating Droplets by Electrowetting-Based Techniques," issued on Jun. 28, 2005; Pamula et al., U.S. Patent Pub. No. 20060194331, entitled "Apparatuses and Methods for Manipulating Droplets on a Printed Circuit Board," published on Aug. 31, 2006; Pollack et al., International Patent Pub. No. WO/2007/120241, entitled "Droplet-Based Biochemistry," published on Oct. 25, 2007; Shenderov, U.S. Pat. No. 6,773,566, entitled "Electrostatic Actuators for Microfluidics and Methods for Using Same," issued on Aug. 10, 2004; Shenderov, U.S. Pat. No. 6,565,727, entitled "Actuators for Microfluidics Without Moving Parts," issued on May 20, 2003; Kim et al., U.S. Patent Pub. No. 20030205632, entitled "Electrowetting-driven Micropumping," published on Nov. 6, 2003; Kim et al., U.S. Patent Pub. No. 20060164490, entitled "Method and Apparatus for Promoting the Complete Transfer of Liquid Drops from a Nozzle," published on Jul. 27, 2006; Kim et al., U.S. Patent Pub. No. 20070023292, entitled "Small Object Moving on Printed Circuit Board," published on Feb. 1, 2007; Shah et al., U.S. Patent Pub. No. 20090283407, entitled "Method for Using Magnetic Particles in Droplet Microfluidics," published on Nov. 19, 2009; Kim et al., U.S. Patent Pub. No. 20100096266, entitled "Method and Apparatus for Real-time Feedback Control of Electrical Manipulation of Droplets on Chip," published on Apr. 22, 2010; Velev, U.S. Pat. No. 7,547,380, entitled "Droplet Transportation Devices and Methods Having a Fluid Surface," issued on Jun. 16, 2009; Sterling et al., U.S. Pat. No. 7,163,612, entitled "Method, Apparatus and Article for Microfluidic Control via Electrowetting, for Chemical, Biochemical and Biological Assays and the Like," issued on Jan. 16, 2007; Becker et al., U.S. Pat. No. 7,641,779, entitled "Method and Apparatus for Programmable Fluidic Processing," issued on Jan. 5, 2010; Becker et al., U.S. Pat. No. 6,977,033, entitled "Method and Apparatus for Programmable Fluidic Processing," issued on Dec. 20, 2005; Decre et al., U.S. Pat. No. 7,328,979, entitled "System for Manipulation of a Body of Fluid," issued on Feb. 12, 2008; Yamakawa et al., U.S. Patent Pub. No. 20060039823, entitled "Chemical Analysis Apparatus," published on Feb. 23, 2006; Wu, U.S. Patent Pub. No. 20110048951, entitled "Digital Microfluidics Based Apparatus for Heat-exchanging Chemical Processes," published on Mar. 3, 2011; Fouillet et al., U.S. Patent Pub. No. 20090192044, entitled "Electrode Addressing Method," published on Jul. 30, 2009; Fouillet et al., U.S. Pat. No. 7,052,244, entitled "Device for Displacement of Small Liquid Volumes Along a Micro-catenary Line by Electrostatic Forces," issued on May 30, 2006; Marchand et al., U.S. Patent Pub. No. 20080124252, entitled "Droplet Microreactor," published on May 29, 2008; Adachi et al., U.S. Patent Pub. No. 20090321262, entitled "Liquid Transfer Device," published on Dec. 31, 2009; Roux et al., U.S. Patent Pub. No. 20050179746, entitled "Device for Controlling the Displacement of a Drop Between Two or Several Solid Substrates," published on Aug. 18, 2005; and Dhindsa et al., "Virtual Electrowetting Channels: Electronic Liquid Transport with Continuous Channel Functionality," Lab Chip, 10:832-836 (2010), the entire disclosures of which are incorporated herein by reference. Certain droplet actuators will include one or more substrates arranged with a droplet operations gap therebetween and electrodes associated with (e.g., layered on, attached to, and/or embedded in) the one or more substrates and arranged to conduct one or more droplet operations. For example, certain droplet actuators will include a base (or bottom) substrate, droplet operations electrodes associated with the substrate, one or more dielectric layers atop the substrate and/or electrodes, and optionally one or more hydrophobic layers atop the substrate, dielectric layers and/or the electrodes forming a droplet operations surface. A top substrate may also be provided, which is separated from the droplet operations surface by a gap, commonly referred to as a droplet operations gap. Various electrode arrangements on the top and/or bottom substrates are discussed in the above-referenced patents and applications and certain novel electrode arrangements are discussed in the description of the present disclosure. During droplet operations it is preferred that droplets remain in continuous contact or frequent contact with a ground or reference electrode. A ground or reference electrode may be associated with the top substrate facing the gap, the bottom substrate facing the gap, in the gap. Where electrodes are provided on both substrates, electrical contacts for coupling the electrodes to a droplet actuator instrument for controlling or monitoring the electrodes may be associated with one or both plates. In some cases, electrodes on one substrate are electrically coupled to the other substrate so that only one substrate is in contact with the droplet actuator. In one embodiment, a conductive material (e.g., an epoxy, such as MASTER BOND™ Polymer System EP79, available from Master Bond, Inc., Hackensack, N.J.) provides the electrical connection between electrodes on one substrate and electrical paths on the other substrates, e.g., a ground electrode on a top substrate may be coupled to an electrical path on a bottom substrate by such a conductive material. Where multiple substrates are used, a spacer may be provided between the substrates to determine the height of the gap therebetween and define on-actuator dispensing reservoirs. The spacer height may, for example, be at least about 5 μm, 100 μm, 200 μm, 250 μm, 275 μm or more. Alternatively or additionally the spacer height may be at most about 600 μm, 400 μm, 350 μm, 300 μm, or less. The spacer may, for example, be formed of a layer of projections form the top or bottom substrates, and/or a material inserted between the top and bottom substrates. One or more openings may be provided in the one or more substrates for forming a fluid path through which liquid may be delivered into the droplet operations gap. The one or more openings may in some cases be aligned for interaction with one or more electrodes, e.g., aligned such that liquid flowed through the opening will come into sufficient proximity with one or more droplet operations electrodes to permit a droplet operation to be effected by the droplet operations electrodes using the liquid. The base (or bottom) and top substrates may in some cases be formed as one integral component. One or more reference electrodes may be provided on the base (or bottom) and/or top substrates and/or in the gap. Examples of reference electrode arrangements are provided in the above referenced patents and patent applications. In various embodiments, the manipulation of droplets by a droplet actuator may be electrode mediated, e.g., electrowetting mediated or dielectrophoresis mediated or Coulombic force mediated. Examples of other techniques for controlling droplet operations that may be used in the droplet actuators of the present disclosure include using devices that induce hydrodynamic fluidic pressure, such as those that operate on the basis of mechanical principles (e.g. external syringe pumps, pneumatic membrane pumps, vibrating membrane pumps, vacuum devices, centrifugal forces, piezoelectric/ultrasonic pumps and acoustic forces); electrical or magnetic principles (e.g. electroosmotic flow, electrokinetic pumps, ferrofluidic plugs, electrohydrodynamic pumps, attraction or repulsion using magnetic forces and magnetohydrodynamic pumps); thermodynamic principles (e.g. gas bubble generation/ phase-change-induced volume expansion); other kinds of surface-wetting principles (e.g. electrowetting, and opto-electrowetting, as well as chemically, thermally, structurally and radioactively induced surface-tension gradients); gravity; surface tension (e.g., capillary action); electrostatic forces (e.g., electroosmotic flow); centrifugal flow (substrate disposed on a compact disc and rotated); magnetic forces (e.g., oscillating ions causes flow); magnetohydrodynamic forces; and vacuum or pressure differential. In certain embodiments, combinations of two or more of the foregoing techniques may be employed to conduct a droplet operation in a droplet actuator of the present disclosure. Similarly, one or more of the foregoing may be used to deliver liquid into a droplet operations gap, e.g., from a reservoir in another device or from an external reservoir of the droplet actuator (e.g., a reservoir associated with a droplet actuator substrate and a flow path from the reservoir into the droplet operations gap). Droplet operations surfaces of certain droplet actuators of the present disclosure may be made from hydrophobic materials or may be coated or treated to make them hydrophobic. For example, in some cases some portion or all of the droplet operations surfaces may be derivatized with low surface-energy materials or chemistries, e.g., by deposition or using in situ synthesis using compounds such as poly- or per-fluorinated compounds in solution or polymerizable monomers. Examples include TEFLON® AF (available from DuPont, Wilmington, Del.), members of the cytop family of materials, coatings in the FLUOROPEL® family of hydrophobic and superhydrophobic coatings (available from Cytonix Corporation, Beltsville, Md.), silane coatings, fluorosilane coatings, hydrophobic phosphonate derivatives (e.g., those sold by Aculon, Inc), and NOVEC™ electronic coatings (available from 3M Company, St. Paul, Minn.), other fluorinated monomers for plasma-enhanced chemical vapor deposition (PECVD), and organosiloxane (e.g., SiOC) for PECVD. In some cases, the droplet operations surface may include a hydrophobic coating having a thickness ranging from about 10 nm to about 1,000 nm. Moreover, in some embodiments, the top substrate of the droplet actuator includes an electrically conducting organic polymer, which is then coated with a hydrophobic coating or otherwise treated to make the droplet operations surface hydrophobic. For example, the electrically conducting organic polymer that is deposited onto a plastic substrate may be poly(3,4-ethylenedioxythiophene) poly(styrenesulfonate) (PEDOT: PSS). Other examples of electrically conducting organic polymers and alternative conductive layers are described in Pollack et al., International Patent Pub. No. WO/2011/002957, entitled "Droplet Actuator Devices and Methods," published on Jan. 6, 2011, the entire disclosure of which is incorporated herein by reference. One or both substrates may be fabricated using a printed circuit board (PCB), glass, indium tin oxide (ITO)-coated glass, and/or semiconductor materials as the substrate. When the substrate is ITO-coated glass, the ITO coating is preferably a thickness of at least about 20 nm, 50 nm, 75 nm, 100 nm or more. Alternatively or additionally the thickness can be at most about 200 nm, 150 nm, 125 nm or less. In some cases, the top and/or bottom substrate includes a PCB substrate that is coated with a dielectric, such as a polyimide dielectric, which may in some cases also be coated or otherwise treated to make the droplet operations surface hydrophobic. When the substrate includes a PCB, the following materials are examples of suitable materials: MITSUI™ BN-300 (available from MITSUI Chemicals America, Inc., San Jose Calif.); ARLON™ 11N (available from Arlon, Inc, Santa Ma, Calif.); NELCO® N4000-6 and N5000-30/32 (available from Park Electrochemical Corp., Melville, N.Y.); ISOLA™ FR406 (available from Isola Group, Chandler, Ariz.), especially IS620; fluoropolymer family (suitable for fluorescence detection since it has low background fluorescence); polyimide family; polyester; polyethylene naphthalate; polycarbonate; polyetheretherketone; liquid crystal polymer; cyclo-olefin copolymer (COC); cyclo-olefin polymer (COP); aramid; THERMOUNT® nonwoven aramid reinforcement (available from DuPont, Wilmington, Del.); NOMEX® brand fiber (available from DuPont, Wilmington, Del.); and paper. Various materials are also suitable for use as the dielectric component of the substrate. Examples include: vapor deposited dielectric, such as PARYLENE™ C (especially on glass), PARYLENE™ N, and PARYLENE™ HT (for high temperature, ~300° C.) (available from Parylene Coating Services, Inc., Katy, Tex.); TEFLON® AF coatings; cytop; soldermasks, such as liquid photoimageable soldermasks (e.g., on PCB) like TAIYO™ PSR4000 series, TAIYO™ PSR and AUS series (available from Taiyo America, Inc.

Carson City, Nev.) (good thermal characteristics for applications involving thermal control), and PROBIMER™ 8165 (good thermal characteristics for applications involving thermal control (available from Huntsman Advanced Materials Americas Inc., Los Angeles, Calif.); dry film soldermask, such as those in the VACREL® dry film soldermask line (available from DuPont, Wilmington, Del.); film dielectrics, such as polyimide film (e.g., KAPTON® polyimide film, available from DuPont, Wilmington, Del.), polyethylene, and fluoropolymers (e.g., FEP), polytetrafluoroethylene; polyester; polyethylene naphthalate; cyclo-olefin copolymer (COC); cyclo-olefin polymer (COP); any other PCB substrate material listed above; black matrix resin; polypropylene; and black flexible circuit materials, such as DuPont™ Pyralux® HXC and DuPont™ Kapton® MBC (available from DuPont, Wilmington, Del.). Droplet transport voltage and frequency may be selected for performance with reagents used in specific assay protocols. Design parameters may be varied, e.g., number and placement of on-actuator reservoirs, number of independent electrode connections, size (volume) of different reservoirs, placement of magnets/bead washing zones, electrode size, inter-electrode pitch, and gap height (between top and bottom substrates) may be varied for use with specific reagents, protocols, droplet volumes, etc. In some cases, a substrate of the present disclosure may be derivatized with low surface-energy materials or chemistries, e.g., using deposition or in situ synthesis using poly- or per-fluorinated compounds in solution or polymerizable monomers. Examples include TEFLON® AF coatings and FLUOROPEL® coatings for dip or spray coating, other fluorinated monomers for plasma-enhanced chemical vapor deposition (PECVD), and organosiloxane (e.g., SiOC) for PECVD. Additionally, in some cases, some portion or all of the droplet operations surface may be coated with a substance for reducing background noise, such as background fluorescence from a PCB substrate. For example, the noise-reducing coating may include a black matrix resin, such as the black matrix resins available from Toray industries, Inc., Japan. Electrodes of a droplet actuator are typically controlled by a controller or a processor, which is itself provided as part of a system, which may include processing functions as well as data and software storage and input and output capabilities. Reagents may be provided on the droplet actuator in the droplet operations gap or in a reservoir fluidly coupled to the droplet operations gap. The reagents may be in liquid form, e.g., droplets, or they may be provided in a reconstitutable form in the droplet operations gap or in a reservoir fluidly coupled to the droplet operations gap. Reconstitutable reagents may typically be combined with liquids for reconstitution. An example of reconstitutable reagents suitable for use with the methods and apparatus set forth herein includes those described in Meathrel et al., U.S. Pat. No. 7,727,466, entitled "Disintegratable Films for Diagnostic Devices," issued on Jun. 1, 2010, the entire disclosure of which is incorporated herein by reference.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations that are sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to volume of the resulting droplets (i.e., the volume of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. Droplet operations may be electrode-mediated. In some cases, droplet operations are further facilitated by the use of hydrophilic and/or hydrophobic regions on surfaces and/or by physical obstacles. For examples of droplet operations, see the patents and patent applications cited above under the definition of "droplet actuator." Impedance or capacitance sensing or imaging techniques may sometimes be used to determine or confirm the outcome of a droplet operation. Examples of such techniques are described in Sturmer et al., U.S. Patent Pub. No. 20100194408, entitled "Capacitance Detection in a Droplet Actuator," published on Aug. 5, 2010, the entire disclosure of which is incorporated herein by reference. Generally speaking, the sensing or imaging techniques may be used to confirm the presence or absence of a droplet at a specific electrode. For example, the presence of a dispensed droplet at the destination electrode following a droplet dispensing operation confirms that the droplet dispensing operation was effective. Similarly, the presence of a droplet at a detection spot at an appropriate step in an assay protocol may confirm that a previous set of droplet operations has successfully produced a droplet for detection. Droplet transport time can be quite fast. For example, in various embodiments, transport of a droplet from one electrode to the next may exceed about 1 sec, or about 0.1 sec, or about 0.01 sec, or about 0.001 sec. In one embodiment, the electrode is operated in AC mode but is switched to DC mode for imaging. It is helpful for conducting droplet operations for the footprint area of droplet to be similar to electrowetting area; in other words, 1×-, 2×-3×-droplets are usefully controlled operated using 1, 2, and 3 electrodes, respectively. If the droplet footprint is greater than number of electrodes available for conducting a droplet operation at a given time, the difference between the droplet size and the number of electrodes should typically not be greater than 1; in other words, a 2× droplet is usefully controlled using 1 electrode and a 3× droplet is usefully controlled using 2 electrodes. When droplets include beads, it is useful for droplet size to be equal to the number of electrodes controlling the droplet, e.g., transporting the droplet.

"Filler fluid" means a fluid associated with a droplet operations substrate of a droplet actuator, which fluid is sufficiently immiscible with a droplet phase to render the droplet phase subject to electrode-mediated droplet operations. For example, the droplet operations gap of a droplet actuator is typically filled with a filler fluid. The filler fluid may, for example, be or include a low-viscosity oil, such as silicone oil or hexadecane filler fluid. The filler fluid may be or include a halogenated oil, such as a fluorinated or perfluorinated oil. The filler fluid may fill the entire gap of the droplet actuator or may coat one or more surfaces of the droplet actuator. Filler fluids may be conductive or nonconductive. Filler fluids may be selected to improve droplet operations and/or reduce loss of reagent or target substances from droplets, improve formation of microdroplets, reduce cross contamination between droplets, reduce contamination of droplet actuator surfaces, reduce degradation of droplet actuator materials, etc. For example, filler fluids may be selected for compatibility with droplet actuator materials. As an example, fluorinated filler fluids may be usefully employed with fluorinated surface coatings. Fluorinated filler fluids are useful to reduce loss of lipophilic compounds, such as umbelliferone substrates like 6-hexadecanoylamido-4-methylumbelliferone substrates (e.g., for use in Krabbe, Niemann-Pick, or other assays); other umbelliferone substrates are described in Winger et al., U.S. Patent Pub. No. 20110118132, entitled "Enzymatic Assays Using Umbelliferone Substrates with Cyclodextrins in Droplets of Oil," published on May 19, 2011, the entire disclosure of which is incorporated herein by reference. Examples of suitable fluorinated oils include those in the Galden line, such as Galden HT170 (bp=170° C., viscosity=1.8 cSt, density=1.77), Galden HT200 (bp=200 C, viscosity=2.4 cSt, d=1.79), Galden HT230 (bp=230 C, viscosity=4.4 cSt, d=1.82) (all from Solvay Solexis); those in the Novec line, such as Novec 7500 (bp=128 C, viscosity=0.8 cSt, d=1.61), Fluorinert FC-40 (bp=155° C., viscosity=1.8 cSt, d=1.85), Fluorinert FC-43 (bp=174° C., viscosity=2.5 cSt, d=1.86) (both from 3M). In general, selection of perfluorinated filler fluids is based on kinematic viscosity (<7 cSt is preferred, but not required), and on boiling point (>150° C. is preferred, but not required, for use in DNA/RNA-based applications (PCR, etc.)). Filler fluids may, for example, be doped with surfactants or other additives. For example, additives may be selected to improve droplet operations and/or reduce loss of reagent or target substances from droplets, formation of microdroplets, cross contamination between droplets, contamination of droplet actuator surfaces, degradation of droplet actuator materials, etc. Composition of the filler fluid, including surfactant doping, may be selected for performance with reagents used in the specific assay protocols and effective interaction or non-interaction with droplet actuator materials. Examples of filler fluids and filler fluid formulations suitable for use with the methods and apparatus set forth herein are provided in Srinivasan et al, International Patent Pub. No. WO/2010/027894, entitled "Droplet Actuators, Modified Fluids and Methods," published on Jun. 3, 2010; Srinivasan et al, International Patent Pub. No. WO/2009/021173, entitled "Use of Additives for Enhancing Droplet Operations," published on Feb. 12, 2009; Sista et al., International Patent Pub. No. WO/2008/098236, entitled "Droplet Actuator Devices and Methods Employing Magnetic Beads," published on Jan. 15, 2009; and Monroe et al., U.S. Patent Pub. No. 20080283414, entitled "Electrowetting Devices," published on Nov. 20, 2008, the entire disclosures of which are incorporated herein by reference, as well as the other patents and patent applications cited herein. Fluorinated oils may in some cases be doped with fluorinated surfactants, e.g., Zonyl FSO-100 (Sigma-Aldrich) and/or others. A filler fluid is typically a liquid. In some embodiments, a filler gas can be used instead of a liquid.

"Immobilize" with respect to magnetically responsive beads, means that the beads are substantially restrained in position in a droplet or in filler fluid on a droplet actuator. For example, in one embodiment, immobilized beads are sufficiently restrained in position in a droplet to permit execution of a droplet splitting operation, yielding one droplet with substantially all of the beads and one droplet substantially lacking in the beads.

"Magnetically responsive" means responsive to a magnetic field. "Magnetically responsive beads" include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, CoO, NiO, $Mn_2O_3$, $Cr_2O_3$, and CoMnP.

"Reservoir" means an enclosure or partial enclosure configured for holding, storing, or supplying liquid. A droplet actuator system of the present disclosure may include on-cartridge reservoirs and/or off-cartridge reservoirs. On-cartridge reservoirs may be (1) on-actuator reservoirs, which are reservoirs in the droplet operations gap or on the droplet operations surface; (2) off-actuator reservoirs, which are reservoirs on the droplet actuator cartridge, but outside the droplet operations gap, and not in contact with the droplet operations surface; or (3) hybrid reservoirs which have on-actuator regions and off-actuator regions. An example of an off-actuator reservoir is a reservoir in the top substrate. An off-actuator reservoir is typically in fluid communication with an opening or flow path arranged for flowing liquid from the off-actuator reservoir into the droplet operations gap, such as into an on-actuator reservoir. An off-cartridge reservoir may be a reservoir that is not part of the droplet actuator cartridge at all, but which flows liquid to some portion of the droplet actuator cartridge. For example, an off-cartridge reservoir may be part of a system or docking station to which the droplet actuator cartridge is coupled during operation. Similarly, an off-cartridge reservoir may be a reagent storage container or syringe which is used to force fluid into an on-cartridge reservoir or into a droplet operations gap. A system using an off-cartridge reservoir will typically include a fluid passage means whereby liquid may be transferred from the off-cartridge reservoir into an on-cartridge reservoir or into a droplet operations gap.

"Transporting into the magnetic field of a magnet," "transporting towards a magnet," and the like, as used herein to refer to droplets and/or magnetically responsive beads within droplets, is intended to refer to transporting into a region of a magnetic field capable of substantially attracting magnetically responsive beads in the droplet. Similarly, "transporting away from a magnet or magnetic field," "transporting out of the magnetic field of a magnet," and the like, as used herein to refer to droplets and/or magnetically responsive beads within droplets, is intended to refer to transporting away from a region of a magnetic field capable of substantially attracting magnetically responsive beads in the droplet, whether or not the droplet or magnetically responsive beads is completely removed from the magnetic field. It will be appreciated that in any of such cases described herein, the droplet may be transported towards or away from the desired region of the magnetic field, and/or the desired region of the magnetic field may be moved towards or away from the droplet. Reference to an electrode, a droplet, or magnetically responsive beads being "within" or "in" a magnetic field, or the like, is intended to describe a situation in which the electrode is situated in a manner which permits the electrode to transport a droplet into and/or away from a desired region of a magnetic field, or the droplet or magnetically responsive beads is/are situated in a desired region of the magnetic field, in each case where the magnetic field in the desired region is capable of substantially attracting any magnetically responsive beads in the droplet. Similarly, reference to an electrode, a droplet, or magnetically responsive beads being "outside of" or "away from" a magnetic field, and the like, is intended to describe a situation in which the electrode is situated in a manner which permits the electrode to transport a droplet away from a certain region of a magnetic field, or the droplet or magnetically responsive beads is/are situated away from a certain region of the magnetic field, in each case where the magnetic field in such region is not capable of substantially attracting any magnetically responsive beads in the droplet or in which any remaining attraction does not eliminate the effectiveness of droplet operations conducted in the region. In various aspects of the present disclosure, a system, a droplet actuator, or another component of a system may include a magnet, such as one or more permanent magnets (e.g., a single cylindrical or bar magnet or an array of such magnets, such as a Halbach array) or an electromagnet or array of electromagnets, to form a magnetic field for interacting with magnetically responsive beads or other components on chip. Such interactions may, for example, include substantially immobilizing or restraining movement or flow of magnetically responsive beads during storage or in a droplet during a droplet operation or pulling magnetically responsive beads out of a droplet.

"Washing" with respect to washing a bead means reducing the amount and/or concentration of one or more substances in contact with the bead or exposed to the bead from a droplet in contact with the bead. The reduction in the amount and/or concentration of the substance may be partial, substantially complete, or even complete. The substance may be any of a wide variety of substances; examples include target substances for further analysis, and unwanted substances, such as components of a sample, contaminants, and/or excess reagent. In some embodiments, a washing operation begins with a starting droplet in contact with a magnetically responsive bead, where the droplet includes an initial amount and initial concentration of a substance. The washing operation may proceed using a variety of droplet operations. The washing operation may yield a droplet including the magnetically responsive bead, where the droplet has a total amount and/or concentration of the substance which is less than the initial amount and/or concentration of the substance. Examples of suitable washing techniques are described in Pamula et al., U.S. Pat. No. 7,439,014, entitled "Droplet-Based Surface Modification and Washing," issued on Oct. 21, 2008, the entire disclosure of which is incorporated herein by reference.

The terms "top," "bottom," "over," "under," and "on" are used throughout the description with reference to the relative positions of components of the droplet actuator, such as relative positions of top and bottom substrates of the droplet actuator. It will be appreciated that the droplet actuator is functional regardless of its orientation in space.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface. In one example, filler fluid can be considered as a film between such liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

Embodiments include a system configured to change the concentration of one or more input droplets and methods for the same. The process of changing the concentration of the input droplet(s) may include using a computationally efficient method of concentration-adjustment on a droplet actuator. Using the presently disclosed embodiments, the storage requirements on a droplet actuator may be reduced while providing a sufficient processing speed. Namely, given a sample liquid having any starting concentration of a substance-of-interest (e.g., genetic material), a concentration-adjustment process is provided for processing the input liquid and achieving a selected target concentration (or ending concentration). The presently disclosed concentration-adjustment process can be useful for any protocols in a droplet actuator, such as, but not limited to, biochemical protocols, affinity-based assay protocols, enzymatic assay protocols, nucleic acid sequencing protocols, polypeptide sequencing protocols and/or protocols for analyses of biological fluids.

In one embodiment, a concentration-adjustment algorithm is provided on a controller of a microfluidics system for processing the sample liquid on a droplet actuator in order to provide a sample liquid that is optimized to a selected target concentration. Optionally, the concentration-adjustment algorithm may be stored in memory as programmed instructions. The controller may be configured to execute the programmed instructions stored to perform the algorithm.

In one example, in a DNA sequencing process the concentration-adjustment algorithm can be used in the library preparation step. Often multiple samples are mixed together for sequencing applications, for example, to improve efficiency of reagent usage and speed of sample processing. For example, for one sequencing run, multiple samples can be mixed together and processed. However, for many DNA sequencing embodiments, each of the multiple samples should contain about the same concentration of genetic material. If, for example, one sample contains 600 nM of genetic material and another sample contains 2 nM of genetic material, then the detector may not be able to collect sufficient signal from the 2 nM-sample or may be saturated by signal from the 600 nM sample. The presently disclosed microfluidics system and concentration-adjustment process (i.e., using the concentration-adjustment algorithm) provides a mechanism for optimizing two or more samples to about the same concentration of genetic material prior to processing.

FIG. 1 illustrates a functional block diagram of an example of a microfluidics system 100 for performing a concentration-adjustment process on a droplet actuator, such as a droplet actuator 105. Digital microfluidic technology conducts droplet operations on discrete droplets in a droplet actuator, such as droplet actuator 105, by electrical control of their surface tension (i.e., electrowetting). The droplets may be sandwiched between two substrates of droplet actuator 105, a bottom substrate and a top substrate separated by a droplet operations gap. The bottom substrate may include an arrangement of electrically addressable electrodes. The top substrate may include a reference electrode plane made, for example, from conductive ink or indium tin oxide (ITO). The bottom substrate and the top substrate may be coated with a hydrophobic material. Droplet operations are conducted in the droplet operations gap. The space around the droplets (i.e., the gap between bottom and top substrates) may be filled with an immiscible inert fluid, such as silicone oil, to prevent evaporation of the droplets and to facilitate their transport within the device. Other droplet operations may be effected by varying the patterns of voltage activation; examples include merging, splitting, mixing, and dispensing of droplets.

Droplet actuator 105 may be designed to fit onto an instrument deck (not shown) of microfluidics system 100. The instrument deck may hold droplet actuator 105 and house other droplet actuator features, such as, but not limited to, one or more magnets and one or more heating devices. For example, the instrument deck may house one or more magnets 110, which may be permanent magnets. Optionally, the instrument deck may house one or more electromagnets 115. Magnets 110 and/or electromagnets 115 are positioned in relation to droplet actuator 105 for immobilization of magnetically responsive beads. Optionally, the positions of magnets 110 and/or electromagnets 115 may be controlled by a motor 120. Additionally, the instrument deck may house one or more heating devices 125 for controlling the temperature within, for example, certain reaction and/or washing zones of droplet actuator 105. In one example, heating devices 125 may be heater bars that are positioned in relation to droplet actuator 105 for providing thermal control thereof.

A controller 130 of microfluidics system 100 is electrically coupled to various hardware components of the apparatus set forth herein, such as droplet actuator 105, electromagnets 115, motor 120, and heating devices 125, as well as to a detector 135, an impedance sensing system 140, and any other input and/or output devices, such as an input device 122. The input device 122 may be any device that is capable of receiving user inputs. The input device 122 may be operably coupled to, for example, a user interface having a display. The input device 122 may include at least one of a keyboard, a mouse, a tracking button, or a touchpad. In some embodiments, the display and the input device 122 may be combined into a touch-sensitive screen. The input device 122 may enable a user to, for example, identify values of designated parameters (e.g., starting concentration or desired concentration).

In one example, detector 135 may be an imaging system that is positioned in relation to droplet actuator 105. In one example, the imaging system may include one or more light-emitting diodes (LEDs) (i.e., an illumination source) and a digital image capture device, such as a charge-coupled device (CCD) camera. Detection can be carried out using an apparatus suited to a particular reagent or label in use. For example, an optical detector such as a fluorescence detector, absorbance detector, luminescence detector or the like can be used to detect appropriate optical labels. Exemplary detectors that can be useful are set forth in US Pat. App. Pub. Nos. 2008/0108082 A1 or 2009/0272914 A1; U.S. Pat. Nos. 7,057,026; 7,329,492; 7,211,414; 7,315,019 7,405,281, or 8,039,817; Bentley et al., *Nature* 456:53-59 (2008), WO 04/018497; WO 91/06678; or WO 07/123744, each of which is incorporated herein by reference.

Impedance sensing system 140 may be any circuitry for detecting impedance at a specific electrode of droplet actuator 105. In one example, impedance sensing system 140 may be an impedance spectrometer. Impedance sensing system 140 may be used to monitor the capacitive loading of any electrode, such as any droplet operations electrode, with or without a droplet thereon. For examples of suitable capacitance detection techniques, see Stunner et al., International Patent Pub. No. WO/2008/101194, entitled "Capacitance Detection in a Droplet Actuator," published on Dec. 30, 2009; and Kale et al., International Patent Pub. No. WO/2002/080822, entitled "System and Method for Dispensing Liquids," published on Feb. 26, 2004, the entire disclosures of which are incorporated herein by reference.

Controller 130 is used to control the overall operations of microfluidics system 100. Controller 130 may, for example, be a general purpose computer, special purpose computer, personal computer, or other programmable data processing apparatus. Controller 130 serves to provide processing capabilities, such as storing, interpreting, and/or executing software instructions, as well as controlling the overall operation of the system. Controller 130 may be configured and programmed to control data and/or power aspects of these devices. For example, in one aspect, with respect to droplet actuator 105, controller 130 controls droplet manipulation by activating/deactivating electrodes. The controller 130 may be or include a processing unit, such as a processing unit described below.

A concentration-adjustment algorithm 150 may reside at or be accessible to the controller 130. Concentration-adjustment algorithm 150 can be implemented in software or hardware and is used to perform a concentration-adjustment process. In some embodiments, the concentration-adjustment process is a process of taking a liquid that has a certain starting concentration of a substance-of-interest and processing the liquid to a different concentration of the substance-of-interest, wherein the ending concentration is selectable. In particular embodiments, the concentration-adjustment process is a process of taking a sample liquid that has a certain starting concentration of genetic material and processing the sample liquid to a different concentration of genetic material, wherein the ending concentration is selectable. Concentration-adjustment algorithm 150 manages a droplet dilution process to take the liquid from a starting concentration to a selected ending (or target) concentration. In one example, the starting concentration of the liquid is about 450 nM and the ending concentration is about 80 nM. In another example, the starting concentration of the liquid is about 325 nM and the ending concentration is about 80 nM.

Concentration-adjustment algorithm 150 is particularly useful in applications in which it may be useful to optimize two or more droplets that have different concentrations (often widely varying) to two or more droplets that have about the same concentration. One such application is a DNA sequencing process. In a DNA sequencing process, the concentration-adjustment algorithm 150 can be used in the library preparation step, wherein often multiple samples are mixed together. Using concentration-adjustment algorithm 150, the multiple samples can be processed on a droplet actuator to about the same concentration, then mixed together, and then sequenced. More details of the presently disclosed concentration-adjustment process that is managed using concentration-adjustment algorithm 150 are shown and described hereinbelow with reference to FIGS. 2, 3, 4, 5, and 6.

The controller 130 may be or include a processing unit. A processing unit includes processing circuitry configured to perform one or more tasks, functions, or steps, such as the methods described herein. For instance, the processing unit may be a logic-based device that performs operations based on instructions stored on a tangible and non-transitory computer readable medium, such as memory. It may be noted that "processing unit," as used herein, is not intended to necessarily be limited to a single processor or single logic-based device. For example, the processing unit may include a single processor (e.g., having one or more cores), multiple discrete processors, one or more application specific integrated circuits (ASICs), and/or one or more field programmable gate arrays (FPGAs). In some embodiments, the processing unit is an off-the-shelf device that is appropriately programmed or instructed to perform operations, such as the algorithms described herein.

The processing unit may also be a hard-wired device (e.g., electronic circuitry) that performs the operations based on hard-wired logic that is configured to perform the algorithms described herein. Accordingly, the processing unit may include one or more ASICs and/or FPGAs. Alternatively or in addition to the above, the processing unit may include or may be associated with a tangible and non-transitory memory having stored thereon instructions configured to direct the processing unit to perform the algorithms described herein.

It is noted that operations performed by the processing unit (e.g., operations corresponding to the methods/algorithms described herein, or aspects thereof) may be sufficiently complex that the operations may not be performed by a human being within a reasonable time period based on the intended application of the assay system. The processing unit may be configured to receive signals from the various sub-systems and devices of the microfluidics system. The processing unit may be configured to perform the droplet operations set forth herein. The processing unit may also be configured to perform the methods.

Processing units may also include or be communicatively coupled to memory. In some embodiments, the memory may include non-volatile memory. For example, the memory may be or include read-only memory (ROM), random-access memory (RAM), electrically erasable programmable read-only memory (EEPROM), flash memory, and the like. The memory may be configured to store data regarding operating parameters of the system.

In the exemplary embodiment, the processing unit executes a set of instructions that are stored in one or more storage elements, memories, or modules in order to at least one of obtain and analyze data. Storage elements may be in the form of information sources or physical memory elements within the system. Embodiments include non-transitory computer-readable media that include set of instructions for performing or executing one or more processes set forth herein. Non-transitory computer readable media may include all computer-readable media, except for transitory propagating signals per se. The non-transitory computer readable media may include generally any tangible computer-readable medium including, for example, persistent memory such as magnetic and/or optical disks, ROM, and PROM and volatile memory such as RAM. The computer-readable medium may store instructions for execution by one or more processors.

The set of instructions may include various commands that instruct the assay system to perform specific operations such as the methods and processes of the various embodiments described herein. The set of instructions may be in the form of a software program. As used herein, the terms "software" and "firmware" can be interchangeable in some embodiments, for example, with respect to including any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

Figure 2:
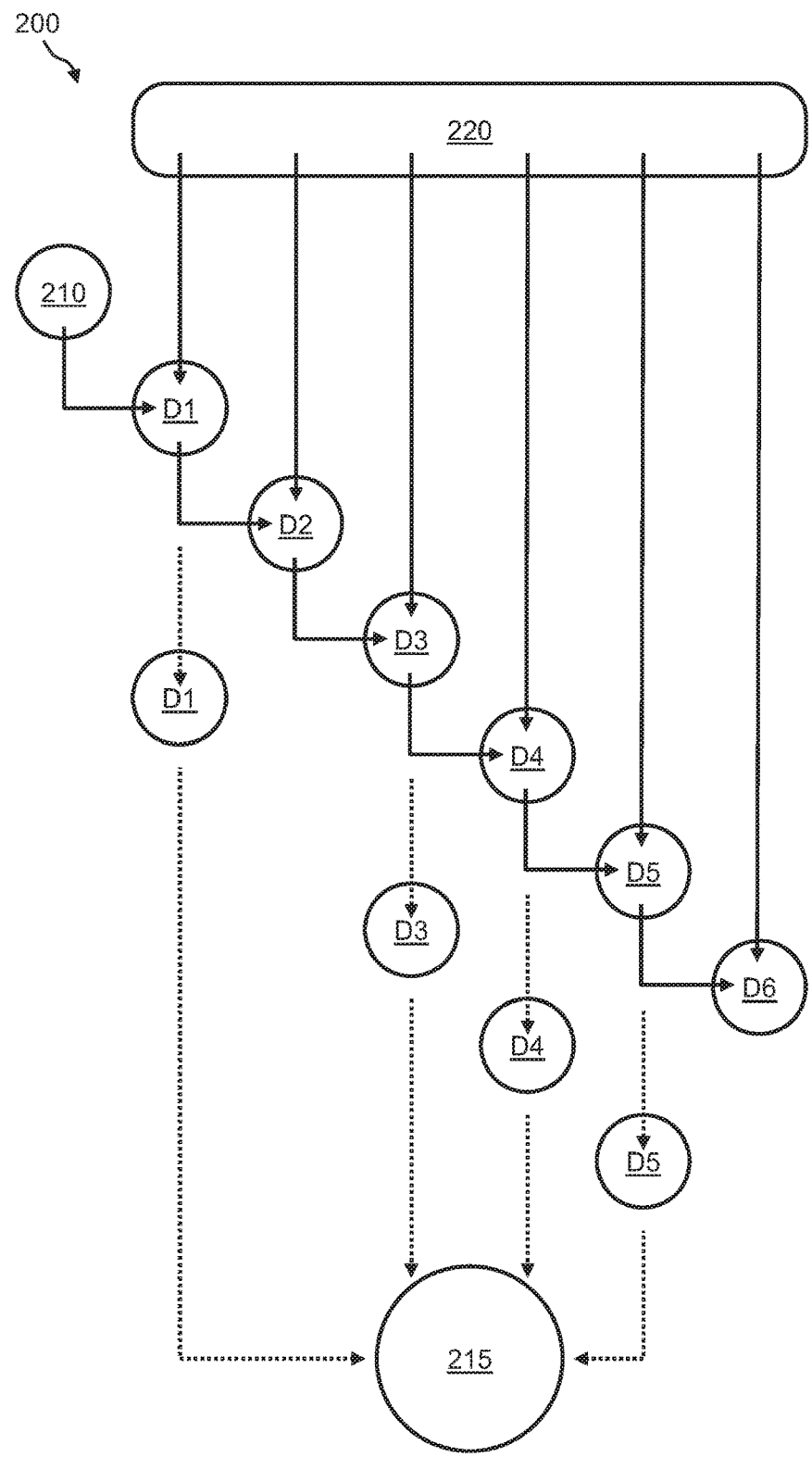
FIG. 2 illustrates a schematic diagram of an example of a concentration-adjustment process through droplet operations.

FIG. 2 illustrates a schematic diagram of an example of the presently disclosed concentration-adjustment process 200, wherein concentration-adjustment process 200 is executed using concentration-adjustment algorithm 150 of microfluidics system 100. In concentration-adjustment process 200, an input droplet (or liquid) 210 is the input droplet to be processed, wherein input droplet 210 has a certain concentration of genetic material. Concentration-adjustment process 200 uses a droplet dilution process to take input droplet 210 of a certain starting concentration and produce an output droplet 215 of a different concentration, wherein output droplet 215 is the droplet that has been optimized and wherein the concentration of output droplet 215 is selectable. In the example shown in FIG. 2, six dilution droplets are generated using a dilution liquid 220. The type of dilution liquid 220 can vary depending on the application. Dilution liquid 220 can be, for example, a reagent or buffer solution.

In the droplet dilution process, the original input droplet 210 is diluted some number of times into some number of dilution droplets, which is selectable. Optionally, the original input droplet 210 is split and one of the split portions is not diluted and another split portion is diluted. After the dilution process, some number of the dilution droplets, which is selectable, are combined to provide the output droplet 215 of a selected target concentration. Optionally, the split input droplet may be combined with one or more of the dilution droplets to provide the output droplet 215.

In particular embodiments, the first dilution droplet is about half the concentration of the original input droplet 210 and each of the subsequent dilution droplets is about half the concentration of the previous dilution droplet. For example, the original input droplet 210 may be split in half and a volume of the dilution liquid that is equal to the volume of the split droplet may be added to one of the split droplets to provide a dilution droplet. As such, the dilution droplet will have a concentration that is 50% of the input droplet 210 or the other split droplet. This process (e.g., splitting the droplet and diluting the split droplet with the dilution liquid) may be repeated one or more times to provide a number dilution droplets plus the split input droplet. In some embodiments, the remaining droplets may include the split droplet (e.g., ½ or other fraction of the input droplet) and 1, 2, 3, 4, 5, 6, 7, 8, 9, 10, 11, 12, 13, 14, 15 or more dilution droplets. These droplets may form a droplet set. The droplet set may or may not include a remainder of the original input droplet 210 (e.g., one of the split droplets from the original input droplet 210).

In particular embodiments, each of the dilution droplets has a common concentration ratio (i.e., the same concentration ratio) with respect to another dilution droplet. For instance, as described above, each dilution droplet may have a concentration that is 50% of the concentration of another dilution droplet. For example, the set of droplets may be the product of a serial dilution. More specifically, a 50% serial dilution series can be carried out to produce a series of droplets that contain 100%, 50%, 25%, 12.5%, 6.25% etc. of the material in the original droplet. An exemplary serial dilution protocol is shown in FIG. 2 and set forth in further detail hereinbelow should be understood, however, that the volume of the dilution liquid that is combined with a droplet may be configured to make the corresponding dilution droplet about any fraction or percentage of the input droplet (or prior dilution droplet). For example, a dilution droplet may have a concentration that is ¾ (75%), ⅔ (66%), ⅗ 60%), ½ (50%), ⅓ (33%), ¼ (25%), or ⅕ (20%) of the input droplet or another dilution droplet.

Moreover, it should be understood that the dilution droplets derived from an input droplet may have different concentration ratios with respect to one another. The example described above includes each dilution droplet having a concentration that is about 50% of a prior droplet. In other embodiments, the concentration ratios may be different. For example, a first dilution droplet may have a concentration that is 50% (or any other percentage or fraction) of the input droplet and a second dilution droplet may have a concentration that is 33% (or any other percentage or fraction) of the first dilution droplet.

FIG. 2 shows, for example, six dilution operations in concentration-adjustment process 200. In this example, a volume of liquid from input droplet 210 and a volume of liquid from dilution liquid 220 are combined to form a dilution droplet D1, wherein dilution droplet D1 is about half the concentration of the original input droplet 210.

Then, a volume of liquid from dilution droplet D1 and a volume of liquid from dilution liquid 220 are combined to form a dilution droplet D2, wherein dilution droplet D2 is about half the concentration of dilution droplet D1.

Then, a volume of liquid from dilution droplet D2 and a volume of liquid from dilution liquid 220 are combined to form a dilution droplet D3, wherein dilution droplet D3 is about half the concentration of dilution droplet D2.

Then, a volume of liquid from dilution droplet D3 and a volume of liquid from dilution liquid 220 are combined to form a dilution droplet D4, wherein dilution droplet D4 is about half the concentration of dilution droplet D3.

Then, a volume of liquid from dilution droplet D4 and a volume of liquid from dilution liquid 220 are combined to form a dilution droplet D5, wherein dilution droplet D5 is about half the concentration of dilution droplet D4.

Then, a volume of liquid from dilution droplet D5 and a volume of liquid from dilution liquid 220 are combined to form a dilution droplet D6, wherein dilution droplet D6 is about half the concentration of dilution droplet D5.

The result of this example dilution process is seven droplets—the original input droplet 210 (which may now have a volume that is half the original volume), dilution droplet D1, dilution droplet D2, dilution droplet D3, dilution droplet D4, and dilution droplet D5, dilution droplet D6. The original input droplet 210 has the highest concentration of the substance-of-interest and the dilution droplet D6 has the lowest concentration of the substance-of-interest.

Once the seven droplets are formed, then some number of the seven droplets are combined to form output droplet 215 of a selected target concentration. FIG. 2 shows, for example, that four of the seven droplets are combined (mixed) to form the output droplet 215 of the selected target concentration. It should be understood, however, that any number of the droplets may be combined, including all of the droplets.

Table 1A and Table 1B below illustrate an EXAMPLE 1 of concentration-adjustment process 200. Table 1A shows the starting concentration of input droplet 210 is 447.871 nM and the resulting concentrations of the dilution droplets D1 through D6. Table 1A also shows the selected target concentration of output droplet 215 to be 81.429 nM. Concentration-adjustment algorithm 150 is used to determine which of the droplets can be mixed (or combined) together to achieve a concentration that is closest to the target concentration of 81.429 nM. In concentration-adjustment algorithm 150, the number of droplets to be mixed is selectable. In EXAMPLE 1, four droplets are selected to be mixed. The four droplets may be automatically selected by the controller 130 using the concentration-adjustment algorithm. Accordingly, concentration-adjustment algorithm 150 is used to determine which droplets can be mixed together to achieve a concentration that is closest to the target concentration (in this example, 81.429 nM). Referring now to Table 1B, concentration-adjustment algorithm 150 selects dilution droplets D1, D3, D4, and D5 to be combined, whereby the resulting actual concentration of output droplet 215 is about 80.477 nM.

TABLE 1A

EXAMPLE 1: Droplet concentrations

| Droplet | Concentration in nM |
|---|---|
| Input droplet 210 | 447.871 |
| Dilution droplet D1 | 223.936 |
| Dilution droplet D2 | 111.968 |
| Dilution droplet D3 | 55.984 |
| Dilution droplet D4 | 27.992 |
| Dilution droplet D5 | 13.996 |
| Dilution droplet D6 | 6.998 |
| Output droplet 215 | 81.429 (target concentration) |

TABLE 1B

EXAMPLE 1: Selected droplets

| Droplet | Concentration in nM |
|---|---|
| Input droplet 210 | 447.871 |
| * Dilution droplet D1 * | * 223.936 * |
| Dilution droplet D2 | 111.968 |
| * Dilution droplet D3 * | * 55.984 * |
| * Dilution droplet D4 * | * 27.992 * |
| * Dilution droplet D5 * | * 13.996 * |
| Dilution droplet D6 | 6.998 |
| Output droplet 215 | 80.477 (actual concentration) |

Table 2A and Table 2B below illustrate an EXAMPLE 2 of concentration-adjustment process 200. Table 2A shows the starting concentration of input droplet 210 is 325.586 nM and the resulting concentrations of the dilution droplets D1 through D6. Table 2A also shows the selected target concentration of output droplet 215 to be 81.429 nM. Concentration-adjustment algorithm 150 is used to determine which of the seven droplets can be mixed (combined) together to achieve a concentration that is closest to the target concentration of 81.429 nM. In concentration-adjustment algorithm 150, the number of droplets to be mixed is selectable. In EXAMPLE 2, the user selects four droplets to be mixed. Accordingly, concentration-adjustment algorithm 150 is used to determine which four of the seven droplets can be mixed together to achieve a concentration that is closest to the target concentration of 81.429 nM. Referring now to Table 2B, concentration-adjustment algorithm 150 selects dilution droplets D1, D2, D3, and D4 to be combined, whereby the resulting actual concentration of output droplet 215 is about 76.309 nM.

TABLE 2A

EXAMPLE 2: Droplet concentrations

| Droplet | Concentration in nM |
| --- | --- |
| Input droplet 210 | 325.586 |
| Dilution droplet D1 | 162.793 |
| Dilution droplet D2 | 81.396 |
| Dilution droplet D3 | 40.698 |
| Dilution droplet D4 | 20.349 |
| Dilution droplet D5 | 10.175 |
| Dilution droplet D6 | 5.087 |
| Output droplet 215 | 81.429 (target concentration) |

TABLE 2B

EXAMPLE 2: Selected droplets

| Droplet | Concentration in nM |
| --- | --- |
| Input droplet 210 | 325.586 |
| * Dilution droplet D1 * | * 162.793 * |
| * Dilution droplet D2 * | * 325.586 * |
| * Dilution droplet D3 * | * 162.793 * |
| * Dilution droplet D4 * | * 81.396 * |
| Dilution droplet D5 | 40.698 |
| Dilution droplet D6 | 5.087 |
| Output droplet 215 | 76.309 (actual concentration) |

More details of how the droplets are selected and how the actual concentration of output droplet 215 is determined are shown and described hereinbelow with reference to FIG. 3.

Further, the number of dilution operations is not limited to six as shown in FIG. 2. This is exemplary only. The number of dilution operations is selectable. Similarly, the number of droplets available for mixing is not limited to seven. Again, this is exemplary only. The number of droplets available for mixing is selectable. Likewise, the number of droplets to be mixed to form the optimized droplet (e.g., output droplet 215) is not limited to four. Again, this is exemplary only. The number of droplets to be mixed is selectable.

In EXAMPLE 1 and EXAMPLE 2, while the starting concentrations of the original samples are different, the two samples are optimized to the same target concentration (e.g., 81.429 nM). This results in two output droplets 215 that have about the same concentration (80.477 nM vs. 76.309 nM), both being near the target concentration of 81.429 nM. Now, the two output droplets 215 that have about the same concentrations can be mixed together and processed, such is in a DNA sequencing process. Accordingly, by using concentration-adjustment process 200, any number of samples can be optimized to a certain target concentration, thereby providing multiple output droplets that have about the same concentration and are suitable for mixing together and processing.

Figure 3:
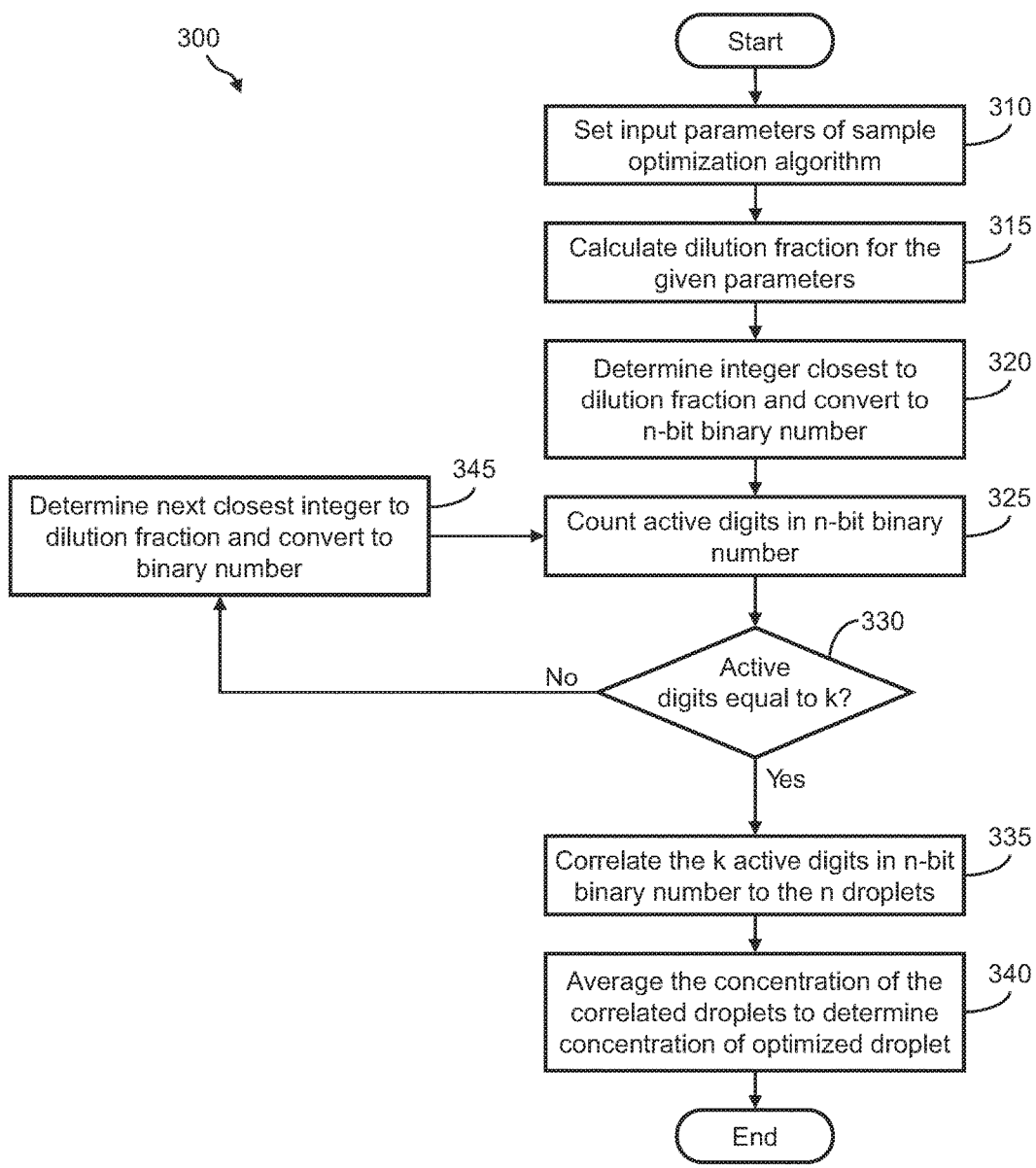
FIG. 3 illustrates a flow diagram of an example of a computationally efficient method of concentration-adjustment on a droplet actuator.

FIG. 3 illustrates a flow diagram of a method 300, which is an example of a computationally efficient method of concentration-adjustment on a droplet actuator using concentration-adjustment algorithm 150. Method 300 may include, but is not limited to, the following steps.

At a step 310, the input parameters of concentration-adjustment algorithm 150 are set. The input parameters of concentration-adjustment algorithm 150 are d, n, k, $C_I$, and $C_O$.

d means the number of times dilution is performed;
n means the number of droplets available for mixing;
k means the number of droplets to be mixed together to form the output droplet;
$C_I$ means the concentration (in nM) of the input sample; and
$C_O$ means the target concentration (in nM) of the output droplet;

A main aspect of microfluidics system 100, concentration-adjustment process 200, and method 300 is that concentration-adjustment algorithm 150 is configurable via the input parameters d, n, k, $C_I$, and $C_O$.

At a step 315, using the parameters d, k, $C_I$, and $C_O$ as described in step 310, concentration-adjustment algorithm 150 calculates a dilution fraction DF, where the dilution fraction DF is calculated according to Equation 1 below.

$$DF = (C_O \times k \times 2^d) \div C_I \quad \text{[Equation 1]}$$

The equation for dilution fraction DF is derived as follows. Also, as used below "concentration" means:

Amount of Solute÷Volume of Solution.

Let V be the volume of droplets 210, D1, D2, D3, D4, D5, and D6. The volume of the output droplet (e.g., output droplet 215) can be expressed as V×k, since it is a mixture of k droplets.

Let $C_I$ be the concentration of the input droplet (e.g., input droplet 210), and $A_I$ be the amount of solute in this droplet. $A_I$ can be expressed as $A_I = C_I \times V$ [Equation A], by definition of concentration.

Let $C_O$ be the target concentration of the output droplet (e.g., output droplet 215), and $A_O$ be its target amount. $A_O$ can be expressed as $A_O = C_O \times V \times k$ [Equation B], again by definition of concentration.

Let $A_F$ be the amount in the final dilution droplet (in EXAMPLE 1 and 2, dilution droplet D6). $A_F$ can be expressed as $A_F = A_I \div 2^d$ since it is the result of splitting $A_I$ in half d times. Applying equation A, gives:

$$A_F = (C_I \times V) \div 2^d \quad \text{[Equation C]}.$$

Notice that the amount in any other droplet is a multiple of $A_F$. Since the output droplet is a sum of these droplets, its amount is a sum of multiples of $A_F$. By the distributive property, this sum is also a multiple of $A_F$.

In the ideal case, this multiple of $A_F$ exactly equals $A_O$. This ideal multiplier can be referred to as the dilution fraction:

$$DF = A_O \div A_F \quad \text{[Equation D]}.$$

In non-ideal real-world cases, the goal is to get the multiplier of $A_F$ as close to the ideal case, DF, as possible. To do this, the value of DF is first computed. Applying equations B and C to equation D, gives:

$$DF = (C_O \times V \times k) \div [(C_I \times V) \div 2^d]$$

Simplifying by moving $2^d$ to the numerator, gives:

$$DF = (C_O \times V \times k \times 2^d) \div (C_I \times V)$$

Simplifying by cancelling V, gives:

$$DF = (C_O \times k \times 2^d) \div C_I \quad \text{[Equation 1]}$$

At a step 320, concentration-adjustment algorithm 150 determines the integer closest to the dilution fraction DF that is calculated in step 315 and then converts the integer to a binary number that includes n number of bits, i.e., converts the integer to an n-bit binary number. For example, if n=7, then concentration-adjustment algorithm 150 converts the integer to a 7-bit binary number.

At a step 325, concentration-adjustment algorithm 150 counts the number of active digits in the n-bit binary number.

At a decision step 330, concentration-adjustment algorithm 150 determines whether the number of active digits in the n-bit binary number is equal to k. For example, if k=4, then concentration-adjustment algorithm 150 determines whether the active digits in the n-bit binary number is equal to 4. If the number of active digits in the n-bit binary number is equal to k, then method 300 proceeds to step 335. However, if the number of active digits in the n-bit binary number is not equal to k, then method 300 proceeds to step 345.

At a step 335, concentration-adjustment algorithm 150 correlates the k active digits in the n-bit binary number to the n droplets. Generally, the least significant bit of the n-bit binary number correlates to the least concentrated dilution droplet and the most significant bit of the n-bit binary number correlates to the most concentrated droplet. For example and referring now to FIG. 4, in concentration-adjustment process 200 of FIG. 2, n=7 and therefore a 7-bit binary number is generated. The least significant bit of the 7-bit binary number correlates to dilution droplet D6 and the most significant bit of the 7-bit binary number correlates to input droplet 210. In one example, with respect to correlating the k active digits in the n-bit binary number to the n droplets, for k=4 and the n-bit binary number 0101011, then the k active digits correspond to dilution droplets D1, D3, D5, and D6.

At a step 340, wherein the k correlated droplets are combined to form the optimized input droplet, concentration-adjustment algorithm 150 averages the concentration of the correlated droplets to determine the concentration of the optimized input droplet, e.g., output droplet 215. Method 300 ends.

At a step 345, concentration-adjustment algorithm 150 determines the next closest integer to the dilution fraction DF that is calculated in step 315 and then converts the integer to a binary number that includes n number of bits, i.e., converts the integer to an n-bit binary number. Method 300 returns to step 325.

A main aspect of method 300 is that the process of iterating through method steps 320, 325, 330, and 345 to rapidly find the integer (when converted to the n-bit binary number) that has k-bits is based on a Peter Wegner algorithm in "A technique for counting ones in a binary computer" (published in Communications of the ACM, Volume 3 Issue 5, May 1960, Page 322). Namely, a main aspect of method 300 is using the Peter Wegner algorithm in a concentration-adjustment process in a digital fluidics application. The following programming code is an example of Wegner's algorithm that can be used in method steps 320, 325, 330, and 345 of method 300.

```
bool HasBitCount(uint v, int desiredCount)
{
    uint count;
    for (count = 0; v > 0; count++)
    {
        if (count >= desiredCount)
        {
            return false;
        }
        v &= v - 1;
    }
    return (count == desiredCount);
}
```

In other embodiments, instead of using the Peter Wegner algorithm in method 300, a lookup table is provided on, for example, controller 130. The lookup table includes the droplets to be combined for any combinations and any values of d, n, k, $C_I$, and $C_O$. A benefit of using the lookup table is processing speed. However, a drawback of using the lookup table is that it may require a large amount of data storage on controller 130.

In one example, method 300 of FIG. 3 can be used to process EXAMPLE 1 of concentration-adjustment process 200 of FIG. 2 as follows.

At step 310, for EXAMPLE 1, the input parameters of concentration-adjustment algorithm 150 are set to d=6, n=7, k=4, $C_I$=447.871 nM, and $C_O$=81.429 nM.

At step 315, using the parameters d, k, $C_I$, and $C_O$ set in step 310, concentration-adjustment algorithm 150 calculates the dilution fraction DF for EXAMPLE 1 according to Equation 1.

$$DF=(C_O \times k \times 2^d) \div C_I$$

$$DF=(81.429 \times 4 \times 2^6) \div 447.871$$

$$DF=20845.824 \div 447.871$$

$$DF=46.544 \qquad \text{[Equation 1]}$$

At step 320, for EXAMPLE 1, concentration-adjustment algorithm 150 determines the integer closest to the dilution fraction DF of 46.544. The closest integer is 47. Then, concentration-adjustment algorithm 150 converts 47 to an n-bit binary number. Because n=7, the integer 47 is converted to a 7-bit binary number, which is 0101111.

At step 325, for EXAMPLE 1, concentration-adjustment algorithm 150 counts the number of active digits in the 7-bit binary number of 0101111. There are 5 active digits in 0101111.

At decision step 330, for EXAMPLE 1, concentration-adjustment algorithm 150 determines whether the number of active digits in the 7-bit binary number is equal to k, which is 4. The number of active digits in the 7-bit binary number is not equal to 4, therefore method 300 proceeds to step 345.

At step 345, for EXAMPLE 1, concentration-adjustment algorithm 150 determines the next closest integer to the dilution fraction DF of 46.544. The next closest integer is 46. Then, concentration-adjustment algorithm 150 converts 46 to an n-bit binary number. Because n=7, the integer 46 is converted to a 7-bit binary number, which is 0101110. Method 300 returns to step 325.

At step 325, for EXAMPLE 1, concentration-adjustment algorithm 150 counts the number of active digits in the 7-bit binary number of 0101110. There are 4 active digits in 0101110.

At decision step 330, for EXAMPLE 1, concentration-adjustment algorithm 150 determines whether the number of active digits in the 7-bit binary number is equal to k, which is 4. The number of active digits in 0101110 is equal to 4, therefore method 300 proceeds to step 335.

Figure 4:
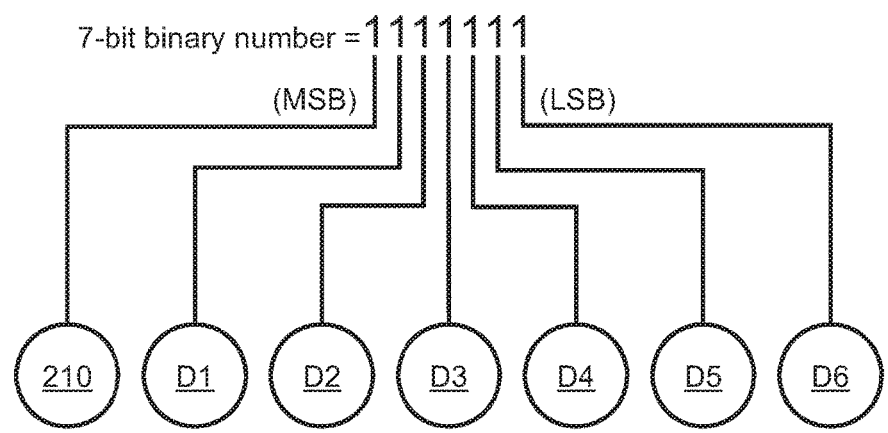
FIG. 4 shows the correlation of the n-bit binary number to the n droplets of the concentration-adjustment process.

At step 335, for EXAMPLE 1, concentration-adjustment algorithm 150 correlates the 4 active digits in 0101110 to the 7 droplets according, for example, to FIG. 4. In this example, the 4 active digits in 0101110 correspond to dilution droplets D1, D3, D4, and D5, which is also shown in Table 1B above.

At step 340, for EXAMPLE 1 and wherein the 4 correlated droplets selected in step 335 are combined to form the optimized input droplet, concentration-adjustment algorithm 150 averages the concentration of dilution droplets D1, D3, D4, and D5 to determine the concentration of the optimized input droplet, e.g., output droplet 215. Referring again to Table 1B, the concentration of output droplet 215 is 80.477 nM. Method 300 ends.

In another example, method 300 of FIG. 3 can be used to process EXAMPLE 2 of concentration-adjustment process 200 of FIG. 2 as follows.

At step 310, for EXAMPLE 2, the input parameters of concentration-adjustment algorithm 150 are set to d=6, n=7, k=4, $C_I$=325.586 nM, and $C_O$=81.429 nM.

At step 315, using the parameters d, k, $C_I$, and $C_O$ set in step 310, concentration-adjustment algorithm 150 calculates the dilution fraction DF for EXAMPLE 2 according to Equation 1.

$$DF=(C_O \times k \times 2^d) \div C_I$$

$$DF=(81.429 \times 4 \times 2^6) \div 325.586$$

$$DF=20845.824 \div 325.586$$

$$DF=64.025 \quad \text{[Equation 1]}$$

At step 320, for EXAMPLE 2, concentration-adjustment algorithm 150 determines the integer closest to the dilution fraction DF of 64.025. The closest integer is 64. Then, concentration-adjustment algorithm 150 converts 64 to an n-bit binary number. Because n=7, the integer 64 is converted to a 7-bit binary number, which is 1000000.

At step 325, for EXAMPLE 2, concentration-adjustment algorithm 150 counts the number of active digits in the 7-bit binary number of 1000000. There is 1 active digit in 1000000.

At decision step 330, for EXAMPLE 2, concentration-adjustment algorithm 150 determines whether the number of active digits in the 7-bit binary number is equal to k, which is 4. The number of active digits in the 7-bit binary number is not equal to 4, therefore method 300 proceeds to step 345.

At step 345, for EXAMPLE 2, concentration-adjustment algorithm 150 determines the next closest integer to the dilution fraction DF of 64.025. The next closest integer is 65. Then, concentration-adjustment algorithm 150 converts 65 to an n-bit binary number. Because n=7, the integer 65 is converted to a 7-bit binary number, which is 1000001. Method 300 returns to step 325.

At step 325, for EXAMPLE 2, concentration-adjustment algorithm 150 counts the number of active digits in the 7-bit binary number of 1000001. There are 2 active digits in 1000001.

At decision step 330, for EXAMPLE 2, concentration-adjustment algorithm 150 determines whether the number of active digits in the 7-bit binary number is equal to k, which is 4. The number of active digits in the 7-bit binary number is not equal to 4, therefore method 300 proceeds to step 345.

Method 300 iterates through steps 345, 325, and 330 for the integers 63, 66, 62, 67, 61, and 68 (in that order) and none have 4 active digits. Then, again at step 345, for EXAMPLE 2, concentration-adjustment algorithm 150 determines the next closest integer to the dilution fraction DF of 64.025. The next closest integer is 60. Then, concentration-adjustment algorithm 150 converts 60 to an n-bit binary number. Because n=7, the integer 60 is converted to a 7-bit binary number, which is 0111100. Method 300 returns to step 325.

At step 325, for EXAMPLE 2, concentration-adjustment algorithm 150 counts the number of active digits in the 7-bit binary number of 0111100. There are 4 active digits in 0111100.

At decision step 330, for EXAMPLE 2, concentration-adjustment algorithm 150 determines whether the number of active digits in the 7-bit binary number is equal to k, which is 4. The number of active digits in 0111100 is equal to 4, therefore method 300 proceeds to step 335.

At step 335, for EXAMPLE 2, concentration-adjustment algorithm 150 correlates the 4 active digits in 0111100 to the 7 droplets according, for example, to FIG. 4. In this example, the 4 active digits in 0111100 correspond to dilution droplets D1, D2, D3, and D4, which is also shown in Table 2B above.

At step 340, for EXAMPLE 2 and wherein the 4 correlated droplets selected in step 335 are combined to form the optimized input droplet, concentration-adjustment algorithm 150 averages the concentration of dilution droplets D1, D2, D3, and D4 to determine the concentration of the optimized input droplet, e.g., output droplet 215. Referring again to Table 2B, the concentration of output droplet 215 is 80.477 nM. Method 300 ends.

Figure 5:
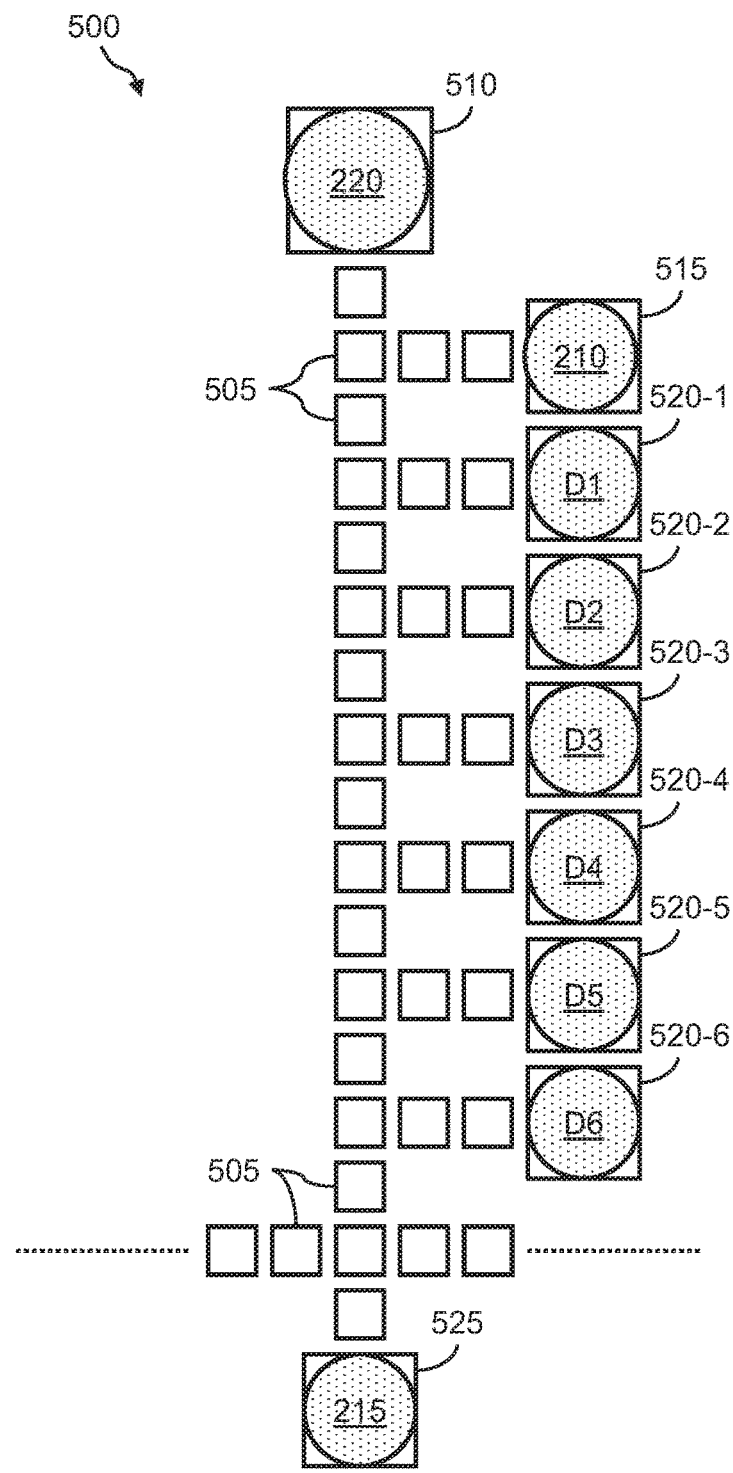
FIG. 5 illustrates a plan view of an example of an electrode arrangement for facilitating the concentration-adjustment process on a droplet actuator.

FIG. 5 illustrates a plan view of an example of an electrode arrangement 500 on a droplet actuator (not shown) for facilitating the concentration-adjustment process 200 and/or method 300. A droplet actuator (not shown) can include a bottom substrate and a top substrate that are separated by a droplet operations gap. The droplet operations gap contains filler fluid, which is, for example, low-viscosity oil, such as silicone oil or hexadecane filler fluid. The bottom substrate may include electrode arrangement 500. The top substrate may include a ground reference plane or electrode. Electrode arrangement 500 includes multiple reservoir electrodes that are fluidly connected via various lines or paths of droplet operations electrodes 505 (e.g., electrowetting electrodes). Droplet operations are conducted atop droplet operations electrodes 505 on a droplet operations surface.

Namely, electrode arrangement 500 includes dilution liquid reservoir electrode 510, a sample liquid reservoir electrode 515, and a plurality of dilution droplet reservoir electrodes 520. Dilution liquid reservoir electrode 510, sample liquid reservoir electrode 515, and the plurality of dilution droplet reservoir electrodes 520 may be associated with on-actuator reservoirs (not shown) of the droplet actuator. FIG. 5 shows dilution liquid 220 atop dilution liquid reservoir electrode 510 and input droplet (or liquid) 210 atop sample liquid reservoir electrode 515.

The number of dilution droplet reservoir electrodes 520 can vary depending on the amount of real estate available on the droplet actuator. In the example shown in FIG. 5, electrode arrangement 500 is designed to support d=6 and n=7, as described in step 310 of method 300 of FIG. 3. Accordingly, electrode arrangement 500 includes six dilution droplet reservoir electrodes 520-1, 520-2, 520-3, 520-4, 520-5, and 520-6. Dilution droplet reservoir electrodes 520-1, 520-2, 520-3, 520-4, 520-5, and 520-6 hold dilution droplets D1, D2, D3, D4, D5, and D6, respectively. Additionally, electrode arrangement 500 includes a collection reservoir electrode 525.

In operation, a volume of dilution liquid 220 is provided atop dilution liquid reservoir electrode 510 and a volume of input droplet (or liquid) 210 is provided atop sample liquid reservoir electrode 515. Input droplet 210 has a certain starting concentration. The starting concentration may be identified by, for example, a user of the system 100. More specifically, the concentration may be determined by receiving user inputs from the user. The user inputs may identify the concentration (e.g., a certain value) or the user inputs may be used to calculate the concentration. In other embodiments, the starting concentration may be determined by the system 100. For example, the input droplet 210 may be measured or may be analyzed using, for example, Biotium quantification protocols or qPCR quantification protocols. One or more protocols for measuring or determining a concentration of a droplet are described in International Application Publication Nos. WO 2014/179596 and WO 2011/057197, each of which is incorporated herein by reference in its entirety.

Using a dilution process as described in concentration-adjustment process 200 and/or method 300, input droplet 210 is processed to form an optimized input droplet, such as output droplet 215, of a selected target concentration. For example, using droplet operations, some amount of input droplet 210 and dilution liquid 220 are mixed at dilution droplet reservoir electrode 520-1 to form dilution droplet D1. Then, some amount of dilution liquid 220 and dilution droplet D1 are mixed at dilution droplet reservoir electrode 520-2 to form dilution droplet D2. Then, some amount of dilution liquid 220 and dilution droplet D2 are mixed at dilution droplet reservoir electrode 520-3 to form dilution droplet D3. Then, some amount of dilution liquid 220 and dilution droplet D3 are mixed at dilution droplet reservoir electrode 520-4 to form dilution droplet D4. Then, some amount of dilution liquid 220 and dilution droplet D4 are mixed at dilution droplet reservoir electrode 520-5 to form dilution droplet D5. Then, some amount of dilution liquid 220 and dilution droplet D5 are mixed at dilution droplet reservoir electrode 520-6 to form dilution droplet D6. In this example, dilution droplet D1 has about half the concentration of genetic material as input droplet 210. Further, each of the dilution droplets has about half the concentration of genetic material as the previous dilution droplet.

Once the dilutions droplets are formed, concentration-adjustment process 200 and/or method 300 can be executed. Then, once the k-number of droplets is selected per step 335 of method 300, the selected droplets are dispensed (via droplet operations) from their respective dilution droplet reservoir electrode 520 and then transported (via droplet operations) to collection reservoir electrode 525. At collection reservoir electrode 525, the selected droplets are mixed together to form the optimized input droplet, such as output droplet 215.

Figure 6:
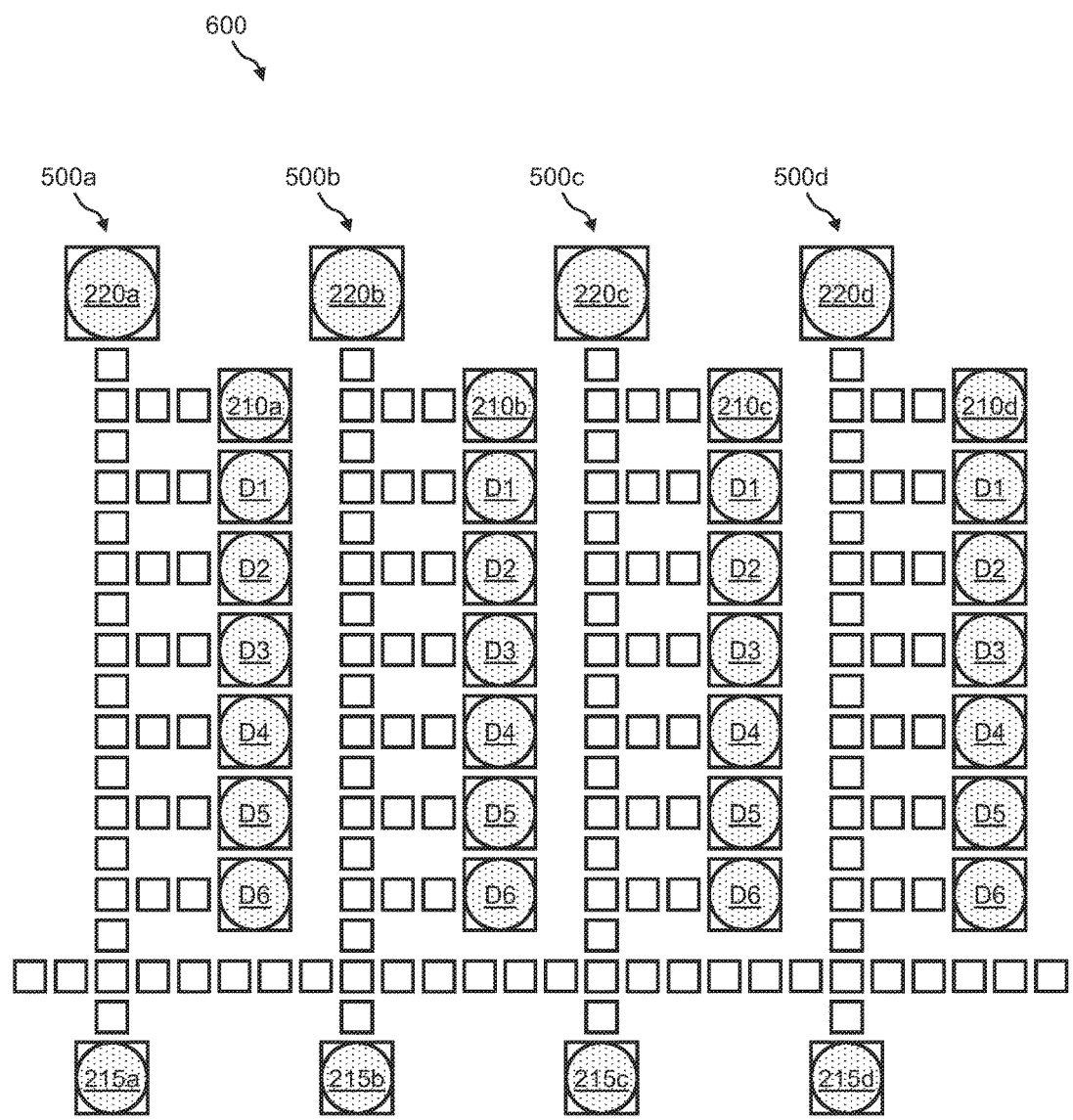
FIG. 6 illustrates a plan view of an example of an electrode arrangement for processing multiple samples on a droplet actuator using the concentration-adjustment process.

To support an application (e.g., a DNA sequencing process) in which it may be useful to optimize two or more samples that have different concentrations (often widely varying) to two or more samples that have about the same concentration, a droplet actuator may include multiple instances of electrode arrangement 500. In one example, FIG. 6 illustrates a plan view of an example of an electrode arrangement 600 on a droplet actuator (not shown) for processing four samples using concentration-adjustment algorithm 150. Electrode arrangement 600 includes four instances of electrode arrangement 500; namely, electrode arrangements 500a, 500b, 500c, and 500d. In this example, the input droplets 210a, 210b, 210c, and 210d have different concentrations $C_I$ of genetic material. Using the concentration-adjustment process 200 and/or method 300, each of the input droplets 210a, 210b, 210c, and 210d is processed using the same target concentration $C_O$. The result is four output droplets 215a, 215b, 215c, and 215d that have about the same concentration. These output droplets 215a, 215b, 215c, and 215d droplets can then be mixed together using droplet operations and sequenced.

In one embodiment, a method is provided that includes providing a droplet actuator having a droplet-operations gap and a plurality of electrodes positioned along the droplet-operations gap. The droplet actuator may be similar or identical to the droplet actuators described herein. The method may also include positioning an input droplet in the droplet-operations gap. It should be understood that "positioning an input droplet" may include receiving an input droplet from an external source, such as a micropipettor, but it may also include generating the input droplet through one or other preparation steps on the droplet actuator.

The method may also include determining a target concentration. The target concentration may be determined before or after receiving the input droplet or before or after forming the dilution droplets. The target concentration may be determined by receiving inputs from an individual (e.g., user inputs) or from a system. In some embodiments, the target concentration may be equal to the concentration of another droplet that will also undergo analysis. In some embodiments, the concentration of the other droplet is known. In other cases, the concentration of the other droplet is not known. In such cases, the concentration may be identified by the user or the system may analyze the droplet to determine the concentration.

Yet in other embodiments, the target concentration does not equal any of the input droplets. For example, a system may receive five input droplets. The target concentration may be a value that is less than each of the input droplets.

The method may also include conducting droplet operations within the droplet-operations gap using the electrodes to generate discrete dilution droplets. The dilution droplets may be formed from the input droplet. For example, the dilution droplets may consist of a volume of the input droplet (or another dilution droplet) and a dilution liquid. In other embodiments, however, other liquids may be combined to the dilution liquid. The set of dilution droplets may have at least two droplets containing different concentrations of the substance-of-interest compared to each other. For example, the concentration of the substances of interest can be different for all droplets in the set. Alternatively, some droplets in a set can be redundant with respect to having the same concentration of the substance of interest. The dilution droplets and, optionally, a remainder of the input droplet (e.g., the input droplet after splitting to form a dilution droplet) may form a droplet set.

The method may also include combining a select number of the droplets from the droplet set to form an output droplet. The select number may be each and every droplet of the droplet set, including the remainder of the input droplet. The select number may also be less than each and every droplet of the droplet det. After combining the select number of the droplets, the output droplet may have a modified concentration of the substance-of-interest that is substantially equal to the target concentration.

It will be appreciated that various aspects of the present disclosure may be embodied as a method, system, computer readable medium, and/or computer program product. Aspects of the present disclosure may take the form of hardware embodiments, software embodiments (including firmware, resident software, micro-code, etc.), or embodiments combining software and hardware aspects that may all generally be referred to herein as a "circuit," "module," or "system." Furthermore, the methods of the present disclosure may take the form of a computer program product on a computer-usable storage medium having computer-usable program code embodied in the medium.

Any suitable computer useable medium may be utilized for software aspects of the present disclosure. The computer-usable or computer-readable medium may be, for example but not limited to, an electronic, magnetic, optical, electro-magnetic, infrared, or semiconductor system, apparatus, device, or propagation medium. The computer readable medium may include transitory and/or non-transitory embodiments. More specific examples (a non-exhaustive list) of the computer-readable medium would include some or all of the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission medium such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

Program code for carrying out operations of the methods and apparatus set forth herein may be written in an object oriented programming language such as Java, Smalltalk, C++ or the like. However, the program code for carrying out operations of the methods and apparatus set forth herein may also be written in conventional procedural programming languages, such as the "C" programming language or similar programming languages. The program code may be executed by a processor, application specific integrated circuit (ASIC), or other component that executes the program code. The program code may be simply referred to as a software application that is stored in memory (such as the computer readable medium discussed above). The program code may cause the processor (or any processor-controlled device) to produce a graphical user interface ("GUI"). The graphical user interface may be visually produced on a display device, yet the graphical user interface may also have audible features. The program code, however, may operate in any processor-controlled device, such as a computer, server, personal digital assistant, phone, television, or any processor-controlled device utilizing the processor and/or a digital signal processor.

The program code may locally and/or remotely execute. The program code, for example, may be entirely or partially stored in local memory of the processor-controlled device. The program code, however, may also be at least partially remotely stored, accessed, and downloaded to the processor-controlled device. A user's computer, for example, may entirely execute the program code or only partly execute the program code. The program code may be a stand-alone software package that is at least partly on the user's computer and/or partly executed on a remote computer or entirely on a remote computer or server. In the latter scenario, the remote computer may be connected to the user's computer through a communications network.

The methods and apparatus set forth herein may be applied regardless of networking environment. The communications network may be a cable network operating in the radio-frequency domain and/or the Internet Protocol (IP) domain. The communications network, however, may also include a distributed computing network, such as the Internet (sometimes alternatively known as the "World Wide Web"), an intranet, a local-area network (LAN), and/or a wide-area network (WAN). The communications network may include coaxial cables, copper wires, fiber optic lines, and/or hybrid-coaxial lines. The communications network may even include wireless portions utilizing any portion of the electromagnetic spectrum and any signaling standard (such as the IEEE 802 family of standards, GSM/CDMA/TDMA or any cellular standard, and/or the ISM band). The communications network may even include powerline portions, in which signals are communicated via electrical wiring. The methods and apparatus set forth herein may be applied to any wireless/wireline communications network, regardless of physical componentry, physical configuration, or communications standard(s).

Certain aspects of present disclosure are described with reference to various methods and method steps. It will be understood that each method step can be implemented by the program code and/or by machine instructions. The program code and/or the machine instructions may create means for implementing the functions/acts specified in the methods.

The program code may also be stored in a computer-readable memory that can direct the processor, computer, or other programmable data processing apparatus to function in a particular manner, such that the program code stored in the computer-readable memory produce or transform an article of manufacture including instruction means which implement various aspects of the method steps.

The program code may also be loaded onto a computer or other programmable data processing apparatus to cause a series of operational steps to be performed to produce a processor/computer implemented process such that the program code provides steps for implementing various functions/acts specified in the methods of the present disclosure.

Figure 7:
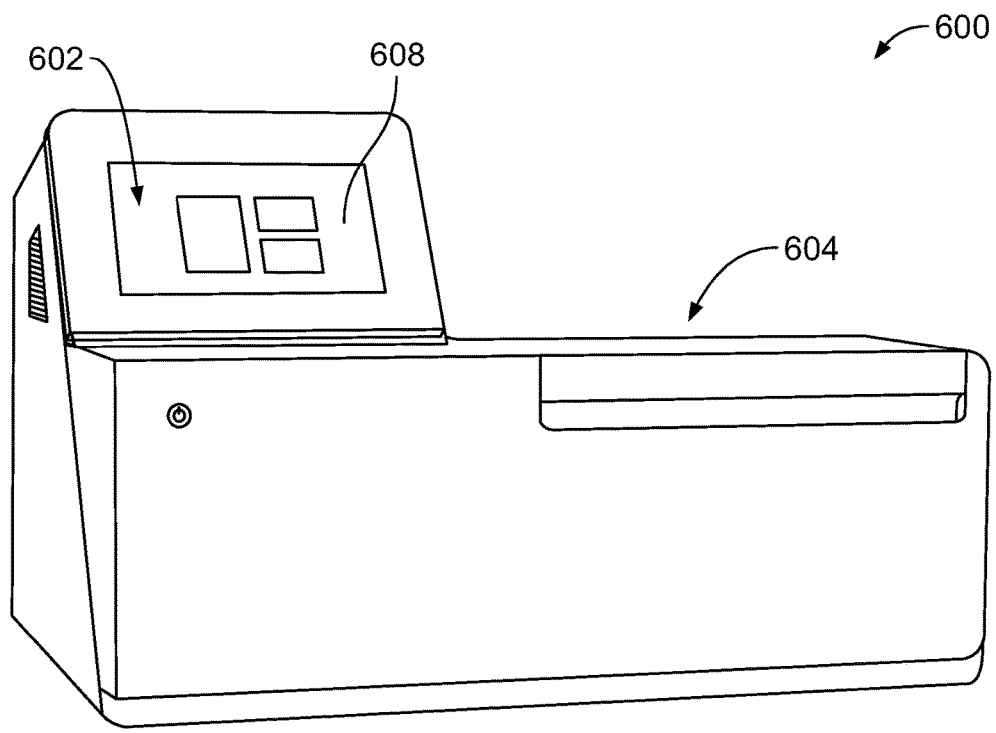
FIG. 7 is a perspective view of a system in accordance with an embodiment that prepares a biological or chemical substance-of-interest for subsequent analysis.

FIG. 7 is a perspective view of a system 600 that prepares a biological or chemical substance-of-interest (e.g., sample) for subsequent analysis. The subsequent analysis, such as sequencing, may also be performed by the system 600. In other embodiments, however, the subsequent analysis may be performed by a separate system. For example, the substance-of-interest may be prepared for subsequent analysis and then removed by a user or machine and delivered to the other system. Among other operations, the system 600 may perform a concentration-adjustment operation, such as the concentration-adjustment processes described above. The system 600 may be similar to the system 100 and include similar or identical components and features.

In particular embodiments, the system 600 receives sample nucleic acids from multiple sources. The nucleic acids from each source may be a different droplet. In particular embodiments, the system 600 amplifies the nucleic acids in each droplet, quantifies the concentration of the nucleic acids in each droplet, and normalizes the concentrations. In some embodiments, the quantifying operation includes integrating quality control information and a standard curve that is generated for each run. In this context, the term "run" includes the library preparation (e.g., A-tailing, amplification) that is performed for each sample droplet. The quality control information may be determined, at least in part, by an optical system (not shown) that is integrated with the system 600. After quantification, the normalizing operation adjusts the concentration of each library to a normalized assay-specific value. When each library has a concentration that is substantially equal to the normalized assay-specific value, the multiple droplets may be combined and the pool may be sequenced. As such, nucleic acids from different sources may be sequenced together.

The system 600 may simultaneously perform these operations on multiple samples. For example, the system 600 may concurrently amplify, quantify, and normalize sixteen (16) different samples. As shown, the system 600 includes a user interface 602 and a loading dock 604 that is configured to receive a droplet actuator, such as the droplet actuator 606 shown in FIG. 8. Similar to the droplet actuator described above, the droplet actuator 606 may include a printed circuit board 610 having a designated array of electrodes (not shown). The droplet actuator 606 also includes a plurality of ports 612 for receiving liquids and permitting liquids to be withdrawn.

Returning to FIG. 7, the user interface 602 includes a touch-sensitive screen 608 that presents a plurality of windows to a user for guiding the user through a designated workflow. For example, the user interface 602 may present a first screen for selecting an assay to perform and a second screen that presents a plurality of settings. Optionally, the system 600 may include a scanner (not shown), such as a barcode scanner, that identifies the assay to be performed based on a code that is associated with the droplet actuator.

The user may select different settings as desired. For example, the settings may include the number of samples (e.g., 0-16 or more), the number of PCR cycles, the insert size, a desired final concentration, and other concentration-adjustment parameters, such as the input parameters described above. Before or after (or during) the user selection operations, the user may load the droplet actuator 606 (FIG. 8) into the loading dock 604. In some embodiments, the user may "walk away" from the system 600, which may automatically carry out the amplification, quantification, and normalization processes without additional user involvement. After the samples have been prepared, quantified, and normalized, the user may remove the samples from the system 600 or the system 600 may carry out a subsequent analysis of the samples.

The following describes one particular application of the system 600. It should be understood, however, that the system 600 may be re-configured or modified (e.g., optically, fluidically, or mechanically) or may be re-programmed to carry out different applications. For example, in some embodiments, the system 600 only normalizes the samples and does not amplify or quantify.

In particular embodiments, the system 600 provides an integrated system for preparing libraries for nucleic acid sequencing. The system 600 utilizes digital microfluidics technology to eliminate many manual steps and prepare samples for sequencing. At least some of the preparation processes include amplification, quantification, and normalization. Quantification may include determining a first concentration of a library (e.g., starting concentration of the library). Normalization may include diluting the library to a target concentration, such as an equimolar or assay-specific concentration. Multiple samples or libraries may be prepared simultaneously. Many or all of the processes for preparing the libraries are conducted on a single droplet actuator, which may also be referred to as a digital microfluidics library card.

Figure 8:
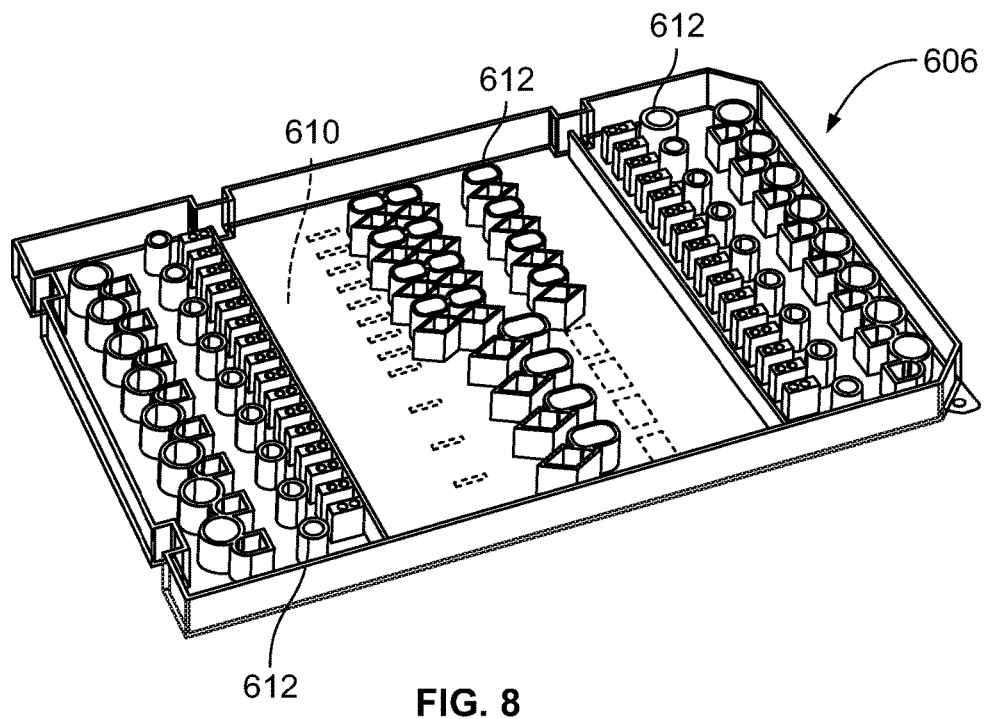
FIG. 8 is an isolated perspective view of a droplet actuator that may be used with the system of FIG. 7.
Figure 9:
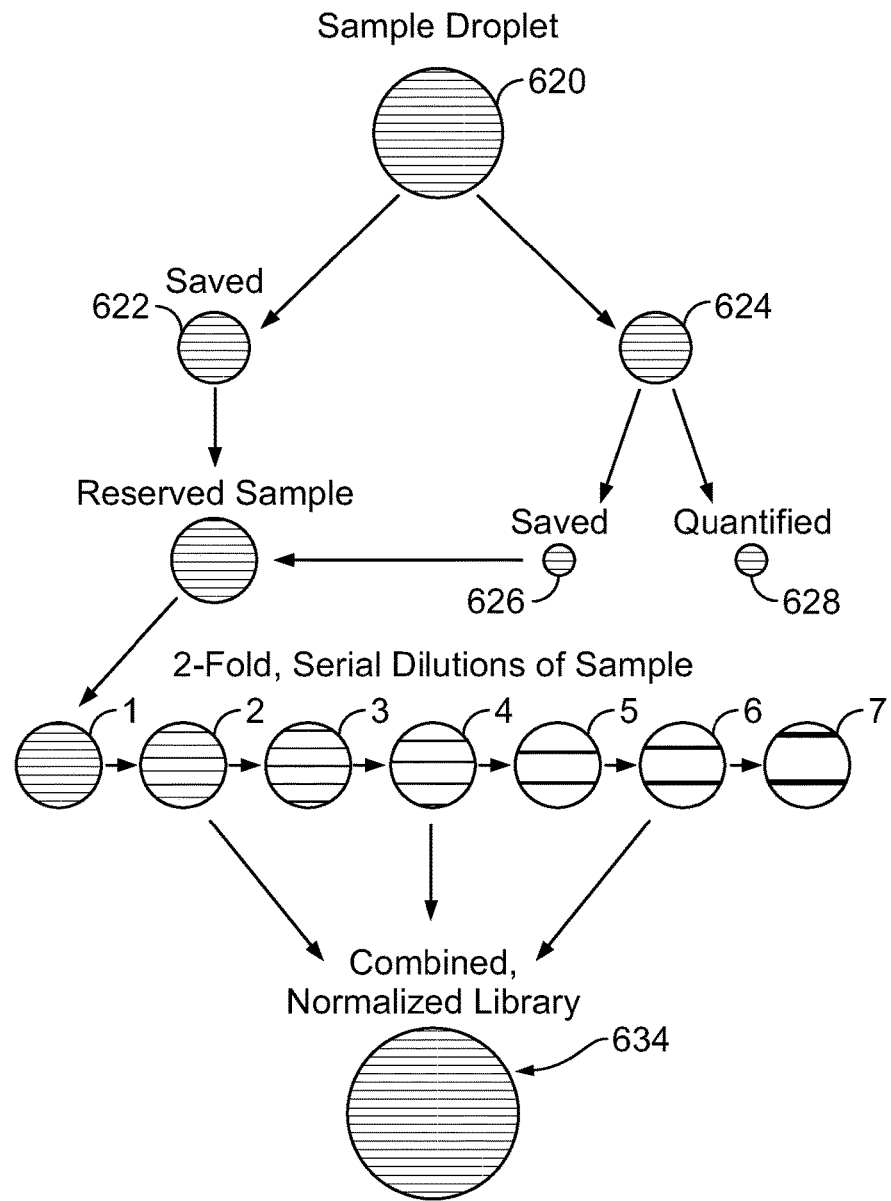
FIG. 9 illustrates how a single sample droplet may be manipulated for a quantification process or operation and a normalization process or operation.

FIG. 9 illustrates how a single sample droplet may be manipulated (e.g., split, mixed, combined, etc.) for a quantification process or operation and a normalization process or operation. These processes may be carried out by the system 600 (FIG. 7) and the droplet actuator 606 (FIG. 8). For each library, a corresponding sample droplet 620 may be split and diluted a plurality of times. As shown in FIG. 9, the sample droplet 620 is separated into a working droplet 624 and a reserved droplet 622. Optionally, the working droplet 624 is diluted by combining the working droplet 624 with a designated volume of a known diluting solution (e.g., water, buffer solution, or the like). The working droplet 624 (or the diluted working droplet) is separated to form a saved droplet 626 and a quantification droplet 628.

The quantification droplet 628 may be analyzed directly (e.g., without further modification) to determine a starting concentration of the sample droplet 620. In an exemplary embodiment, however, the quantification droplet 628 is further modified. For example, the quantification droplet 628 may be mixed with a double-stranded DNA-binding fluorescent dye for optical detection and measurement. Using standards of known concentration, a standard curve may be generated and used to calculate a concentration of the quantification droplet 628. The concentration of the sample droplet 620 is equal to or based on the concentration of the quantification droplet 628. Library concentrations may be calculated in nanograms per microliter (ng/ul) and then converted and reported in nanomolar (nM) or concentrations based on assumed library size. Optionally, the user may select the library size. For example, the system 600 may allow the user to select a designated library concentration prior to the quantification.

The system 600 may have a plurality of optical detectors to analyze the quantification droplet 628. The optical detectors may be calibrated before library preparation to control the variation in measurements among the detectors. Optionally, optical calibration is performed independently for each optical detector. A droplet of a free fluorescent dye with the same emission and excitation spectra as that of the DNA binding dye used in library quantification is dispensed. A single dye droplet of a fixed concentration appropriate for the assay is measured in triplicate at a plurality of different, increasing integration times by each detector. Because the integration time is the same from detector to detector for a fixed dye concentration, the only variable is measured fluorescence.

The data is then plotted in an optical calibration curve and the slope of the best fit line of the data is calculated for each detector. Variation is eliminated by dividing the relative fluorescence measured by any one detector by the slope of the calibration curve for that detector, as a detector that reads higher fluorescence will also have a higher slope.

In some embodiments, measured fluorescence of the calibration dye droplet for the integration time is compared to a designated range of values. As an example, the measured fluorescence should be greater than 20,000 relative fluorescent units (RFUs) and less than 1 million RFUs in some embodiments. Readings below and above this range may indicate that the dye failed to dispense or the photodiode detector was saturated, respectively.

Droplets containing standards of known concentration may be prepared and measured at the same time as library droplets. In some embodiments, the measured fluorescence of standards should be greater than 10,000 RFUs and less than 1,000,000 RFUs. The system may be able to tolerate exclusion of one standard to plot the standard curve for quantification of library droplets. Linear regression of the best fit line should have an $R^2$ that exceeds a designated value (e.g., 0.95 or 0.99) to pass standard curve quality control (QC) reagent loading problems, reagent evaporation, or general fluidics issues adversely affect preparation of the standard curve. The system may not extrapolate from the standard curve metrics; therefore, measured fluorescence of samples that exceed the highest standard will not be quantified by the system and will be reported as "too high to quant."

Again, the above describes an exemplary manner of determining the concentration of a substance-of-interest (or quantifying). Other methods may be used.

After library quantification is complete, the system may normalize the libraries to a target concentration for sequencing using the reserved droplet 622, which may or may not be combined with the saved droplet 626. The target concentration for sequencing may be based on the assay to be performed. As described above the system may make a plurality of serial dilutions of the droplets. For example the system may make a series of seven droplets (labeled as 1-7) of two-fold decreasing concentrations for each library independent of the quantification value. Optionally, the droplets in the series may have other concentrations (e.g., three-fold decreasing concentrations). The system may then select any combination of droplets in the series (e.g., 2, 3, or 4 droplets). Based on the target concentration, a combination of droplets are selected that, when combined, will provide a concentration that is substantially equal to the target concentration (e.g., the normalized assay-specific value). The select number of droplets are then combined to provide an output droplet 634. Optionally, libraries may be quantified using the steps described above after normalization to confirm concentrations. However, in some embodiments, the libraries are not re-quantified. After normalizing, the normalized droplets may be collected and separated from oil for sequencing.

In some embodiments, the system provides a plurality of options for preparing the libraries. For example, the system may simply prepare the libraries (e.g., amplify the samples) without quantification or normalization. The system may prepare the libraries and quantify the libraries without normalization. The system may also prepare the libraries, quantify the libraries, and normalize the libraries. Optionally, the system may be configured to receive samples that were previously prepared (e.g., A-tailed, amplified, ligated) and quantify and/or normalize the sample droplets. In some embodiments, the system may prepare library droplets that have a targeted or designated volume, such as 10 μL.

In some embodiments, the system may be configured to generate a library report, such as the library report shown in FIGS. 10 and 11. FIG. 10 shows a first portion of a library report 630A, and FIG. 11 shows a second portion of the library report 630B. FIG. 12 includes a table 632 that describes how to interpret comments in the library report 630A, 630B and what, if any, actions should be taken.

Figure 13:
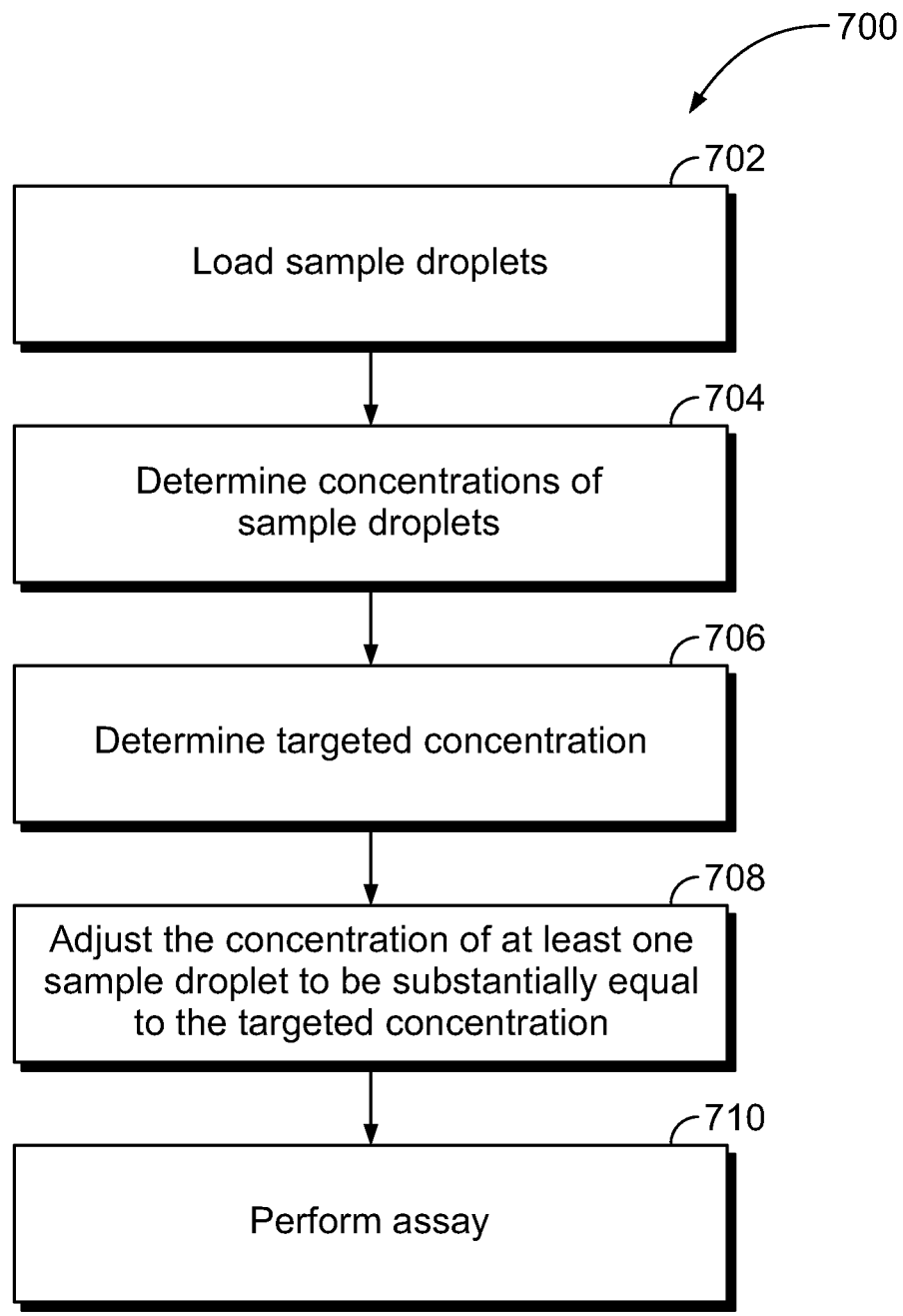
FIG. 13 is a flowchart illustrating a method in accordance with one embodiment.

FIG. 13 is a flowchart illustrating a method 700 in accordance with one embodiment. One or more steps (or all steps) may be performed by embodiments described herein, such as the systems 100 and 600. One or more steps may be performed by other apparatuses or manually by a user. The method 700 includes loading, at 702, sample droplets into, for example, a droplet actuator. The droplet actuator may be similar or identical to the droplet actuators described herein, including the droplet actuators described in the incorporated documents. The droplet actuator has a droplet-operations gap and a plurality of electrodes positioned along the droplet-operations gap. The sample droplets may be held separately from each other in the droplet-operations gap. For example, each of the sample droplets may be loaded into the droplet actuator through a separate port, such as the ports 612. Each of the sample droplets includes a substance of interest, such as nucleic acids (e.g., DNA, RNA). The loading, at 702, may occur when the droplet actuator is operably coupled to a system, such as the system 100 or 600. The loading 702 may be performed automatically by the system or a user may manually deposit the sample droplets into the droplet actuator.

At 704, the concentration of the substance-of-interest in each of the sample droplets may be determined. For example, the substance-of-interest may be determined by analyzing the sample droplet as a whole or by analyzing only a fraction of the sample droplet, such as the quantification droplet 628. As described in the example above, the quantification droplet may be mixed with a fluorescent dye and then detected using, for example, optical detectors (e.g., photodiodes). Emissions that are detected by the optical detectors may be compared to known standards and the concentration may be determined therefrom. In other embodiments, the concentrations may be determined in other manners. Yet in other embodiments, the user may provide user inputs that identify the concentration (e.g., enter values through the user interface).

At 706, the target concentration may be determined. When a plurality of sample droplets are analyzed simultaneously, it may be desirable for the concentration of each of the sample droplets to be substantially equal to a target concentration. The target concentration may be about equal to or less than the lowest concentration that was determined at 704. For example, if the lowest concentration is 80 nM, then the target concentration may be 80 nM or less than 80 nM. The determining operation at 706 may also include receiving user inputs that identify the target concentration.

At 708, the method 700 may include adjusting the respective concentration of at least one of the sample droplets so that each of the respective concentrations of at least a plurality of the sample droplets is substantially equal to a target concentration. For example, if only two or three sample droplets were loaded into the droplet actuator, then it is possible that only one or two of the sample droplets will have concentrations that are significantly different than the target concentration. If several sample droplets (e.g., six or more) are loaded into the droplet actuator, then it is likely that the concentration of more than one sample droplet must be adjusted to be substantially equal to the target concentration.

Adjusting, at 708, the concentration of those sample droplets that should be modified may occur as described above. For example, the adjusting operation may include conducting droplet operations within the droplet-operations gap using the electrodes of the droplet actuator to generate discrete dilution droplets that are formed from (e.g., derived from) the corresponding sample droplet. The dilution droplets and, optionally, a remainder of the corresponding sample droplet may form a droplet set. At least two of the dilution droplets in the droplet set may have different concentrations of the substance-of-interest.

The adjusting operation, at 708, may include combining a select number of the droplets from the droplet set to form an output droplet having a modified concentration. The select number of the droplets may be based on the respective concentration of the corresponding sample droplet and the target concentration. The adjusting operation, at 708, may include identifying the select number of droplets to be combined.

At 710, an assay may be performed using the output droplet and at least one other sample droplet and/or at least one other outlet droplet that is based on another sample droplet. More specifically, it may be necessary to adjust the concentration of other sample droplets so that each of the sample droplets has a concentration that is substantially equal to the target concentration. The adjusting operations may occur concurrently. The assay may be, for example, a sequencing-by-synthesis assay. Optionally, the output droplet may be combined with the other sample droplets or other output droplets to form a sample pool.

In an embodiment, a method is provided that includes providing a droplet actuator having a droplet-operations gap and a plurality of electrodes positioned along the droplet-operations gap. The method also includes positioning first and second input droplets within the droplet-operations gap. The first input droplet has a first concentration of a first sample. The second input droplet has a second concentration of a second sample. The method also includes conducting droplet operations within the droplet-operations gap using the electrodes to generate discrete dilution droplets that are formed from the first input droplet. The dilution droplets and a remainder of the first input droplet form a droplet set. At least two of the dilution droplets in the droplet set have different concentrations of the substance-of-interest. The method also includes combining a select number of the droplets from the droplet set to form an output droplet. The output droplet has a modified concentration of the first sample that is substantially equal to the second concentration of the second sample.

In some aspects, the method may also include performing an assay using the first input droplet and the output droplet. Optionally, the assay may be a sequencing-by-synthesis assay.

In some aspects, each of the dilution droplets may be formed by combining a first volume of a dilution liquid and a second volume of another droplet. The other droplet may be the first input droplet or one of the other dilution droplets.

In some aspects, the first and second volumes may have equal volumes such that the concentration of each dilution droplet is about half the concentration of the other droplet.

In some aspects, the dilution droplets that are selected to be combined may be based on (or a function of) at least one of: (a) a designated number of dilution operations; (b) a designated number of droplets available for combining; (c) a designated number of droplets to be combined together to form the output droplet; (d) the first concentration of the first input droplet; or (e) the second concentration of the second input droplet.

In some aspects, the method also includes identifying the select number of the droplets to be combined based on a dilution fraction (DF), the DF being equal to $(C_O \times k \times 2^d) \div C_I$; wherein d is the number of dilution operations, k is the number of droplets to be combined to form the output droplet, $C_I$ is the first concentration of the first input droplet, and $C_O$ is the second concentration of the second input droplet.

Optionally, identifying the select number of the droplets to be combined may include: (a) identifying an integer that is approximately equal to the DF and converting the integer into an n-bit binary number, wherein n is the number of dilution droplets available for combining; (b) counting a number of active digits in the n-bit binary number; or (c) determining whether the number of active digits is equal to k. If the number of active digits is equal to k, the method includes correlating the active digits of the n-bit binary number to the droplets in the droplet set thereby identifying the droplets to be combined. If the number of active digits does not equal k, the method includes repeating (a)-(c) for a different integer.

In some aspects, the method may also include identifying the select number of the droplets to be combined using a lookup table. The lookup table includes (a) a range of designated concentrations for the first input droplet and (b) a range of designated concentrations for the second input droplet. Optionally, the lookup table also includes at least one of (a) a range of numbers that represent the number of dilution operations that can be performed; (b) a range of numbers that represent the number of droplets available for combining; or (c) a range of numbers that represent the number of droplets to be combined together to form the output droplet. Optionally, the lookup table is populated based on a dilution fraction (DF), the DF being equal to: $(C_O \times k \times 2^d) \div C_I$; wherein d is the number of dilution operations, k is the number of droplets to be combined to form the output droplet, $C_I$ is the concentration of the input droplet, and $C_O$ is the second concentration of the second input droplet.

In some aspects, the method also includes receiving user inputs that designate at least one of (a) a number of times dilution is performed; (b) a number of droplets available for combining; (c) a number of droplets to be combined to form the output droplet; (d) the first concentration of the first input droplet; or (e) the second concentration of the second input droplet.

In some aspects, the method also includes determining the second concentration of the second sample in the second droplet. Optionally, determining the second concentration includes measuring the second concentration in the second droplet. Optionally, determining the second concentration includes analyzing the second droplet to determine the second concentration. Optionally, determining the second concentration includes receiving user inputs to calculate the second concentration. Optionally, determining the second concentration includes receiving user inputs that identify the second concentration. Optionally, the method also includes combining the first and second droplets to form a sample pool. Optionally, the method also includes performing an assay using the sample pool. In an embodiment, a system is provided that includes a droplet actuator having a droplet-operations gap and a plurality of electrodes positioned along the droplet-operations gap. The droplet-operations gap is configured to receive an input droplet. The input droplet has a starting concentration of a substance-of-interest. The system also includes a controller that is operably coupled to the electrodes of the droplet actuator. The controller is configured to control the electrodes to conduct droplet operations within the droplet-operations gap using the electrodes to generate discrete dilution droplets that are formed from the input droplet. The dilution droplets and a remainder of the input droplet form a droplet set. At least two of the dilution droplets in the droplet set have different concentrations of the substance-of-interest. The controller is also configured to control the electrodes to combine a select number of the droplets from the droplet set to form an output droplet, the output droplet having a modified concentration of the substance-of-interest that is substantially equal to a designated target concentration.

In some aspects, the controller is also configured to identify the select number of the droplets to be combined based on a dilution fraction (DF). The DF is equal to $(C_O \times k \times 2^d) \div C_I$, wherein d is the number of dilution operations, k is the number of droplets to be combined together to form the output droplet, $C_1$ is the concentration of the input droplet, and $C_O$ is the target concentration of the output droplet.

Optionally the controller is configured to identify the select number of droplets to be combined by (a) identifying an integer that is approximately equal to the DF and converting the integer into an n-bit binary number, wherein n is the number of dilution droplets available for combining; (b) counting a number of active digits in the n-bit binary number; (c) determining whether the number of active digits is equal to k. If the number of active digits is equal to k, the controller is configured to correlate the active digits of the n-bit binary number to the droplets in the droplet set thereby identifying the droplets to be combined. If the number of active digits does not equal k, the controller is configured to repeat (a)-(c) for a different integer.

In some aspects, the controller identifies the select number of the droplets to be combined by using a lookup table. The lookup table includes (a) a range of designated concentrations for the input droplet and (b) a range of designated concentrations for the output droplet. Optionally, the lookup table also includes at least one of: (a) a range of numbers that represent the number of dilution operations that can be performed; (b) a range of numbers that represent the number of droplets available for mixing; (c) a range of numbers that represent the number of droplets to be combined together to form the output droplet. Optionally, the lookup table is populated based on a dilution fraction (DF). The DF is equal to $(C_O \times k \times 2^d) \div C_I$; wherein d is the number of dilution operations, k is the number of droplets to be combined together to form the output droplet, $C_I$ is the concentration of the input droplet, and $C_O$ is the target concentration of the output droplet.

In some aspects, the controller is configured to receive user inputs that designate at least one of (a) a number of times dilution is performed; (b) a number of droplets available for mixing; (c) a number of droplets to be combined together to form the output droplet; (d) the starting concentration of the input droplet; or (e) the target concentration of the output droplet.

In an embodiment, a system is provided that includes a droplet actuator having a droplet-operations gap and a plurality of electrodes positioned along the droplet-operations gap. The droplet-operations gap is configured to receive an input droplet. The input droplet has a starting concentration of a substance-of-interest. The system also includes a controller that is operably coupled to the electrodes of the droplet actuator. The controller is configured to control the electrodes to conduct droplet operations within the droplet-operations gap using the electrodes to generate discrete dilution droplets that are formed from the first input droplet. The dilution droplets and a remainder of the first input droplet form a droplet set. At least two of the dilution droplets in the droplet set having different concentrations of the substance-of-interest. The controller is also configured to control the electrodes to combine a select number of the droplets from the droplet set to form an output droplet. The output droplet has a modified concentration of the first sample that is substantially equal to the second concentration of the second sample.

In some aspects, the system is configured to perform an assay using the first input droplet and the output droplet. Optionally, the assay is library preparation assay.

In some aspects, each of the dilution droplets is formed by combining a first volume of a dilution liquid and a second volume of another droplet. The other droplet is the first input droplet or one of the other dilution droplets. Optionally, first and second volumes are equal volumes such that the concentration of each dilution droplet is about half the concentration of the other droplet.

In some aspects, the dilution droplets that are selected to be combined are based on at least one of: (a) a designated number of dilution operations; (b) a designated number of droplets available for combining; (c) a designated number of droplets to be combined together to form the output droplet; (d) the first concentration of the first input droplet; or (e) the second concentration of the second input droplet.

In some aspects, the controller is configured to identify the select number of the droplets to be combined based on a dilution fraction (DF), the DF being equal to $(C_O \times k \times 2^d) \div C_I$; wherein d is the number of dilution operations, k is the number of droplets to be combined to form the output droplet, $C_I$ is the first concentration of the first input droplet, and $C_O$ is the second concentration of the second input droplet.

Optionally, the controller is configured to identify the select number of the droplets to be combined by (a) identifying an integer that is approximately equal to the DF and converting the integer into an n-bit binary number, wherein n is the number of dilution droplets available for combining; (b) counting a number of active digits in the n-bit binary number; (c) determining whether the number of active digits is equal to k. If the number of active digits is equal to k, the controller is configured to correlate the active digits of the n-bit binary number to the droplets in the droplet set thereby identifying the droplets to be combined. If the number of active digits does not equal k, the controller is configured to repeat (a)-(c) for a different integer.

In some aspects, the controller is configured to identify the select number of the droplets to be combined using a lookup table. The lookup table includes (a) a range of designated concentrations for the first input droplet and (b) a range of designated concentrations for the second input droplet. Optionally, the lookup table also includes at least one of (a) a range of numbers that represent the number of dilution operations that can be performed; (b) a range of numbers that represent the number of droplets available for combining; or (c) a range of numbers that represent the number of droplets to be combined together to form the output droplet.

Optionally, the lookup table is populated based on a dilution fraction (DF). The DF is equal to $(C_O \times k \times 2^d) \div C_I$, wherein d is the number of dilution operations, k is the number of droplets to be combined to form the output droplet, $C_I$ is the concentration of the input droplet, and $C_O$ is the second concentration of the second input droplet.

In some aspects, the controller is configured to receive user inputs that designate at least one of (a) a number of times dilution is performed; (b) a number of droplets available for combining; (c) a number of droplets to be combined to form the output droplet; (d) the first concentration of the first input droplet; or (e) the second concentration of the second input droplet.

In some aspects, the controller is configured to determine the second concentration of the second sample in the second droplet.

In some aspects, the controller is configured to determine the second concentration by automatically measuring the second concentration in the second droplet. Optionally, the controller is configured to determine the second concentration by automatically analyzing the second droplet to determine the second concentration. Optionally, the controller is configured to determine the second concentration by automatically receiving user inputs to calculate the second concentration. Optionally, the controller is configured to determine the second concentration by automatically receiving user inputs that identify the second concentration. Optionally, the controller is configured to combine the first and second droplets to form a sample pool. Optionally the controller is configured to perform an assay using the sample pool.

In some aspects, the controller is configured to execute programmed instructions stored in memory, wherein the controller, when executing the programmed instructions, conducts the droplet operations and combines the select number of the droplets from the droplet set.

In an embodiment, a method is provided that includes loading sample droplets into a droplet actuator. The droplet actuator has a droplet-operations gap and a plurality of electrodes positioned along the droplet-operations gap. The sample droplets is separated from one another in the droplet-operations gap and including a substance-of-interest. The method also includes determining respective concentrations of the substance-of-interest in the sample droplets and adjusting the respective concentration of at least one of the sample droplets so that each of the respective concentrations of at least a plurality of the sample droplets is substantially equal to a target concentration. Adjusting the respective concentration of a corresponding sample droplet includes conducting droplet operations within the droplet-operations gap using the electrodes to generate discrete dilution droplets that are formed from a corresponding sample droplet. The dilution droplets and a remainder of the corresponding sample droplet form a droplet set. At least two of the dilution droplets in the droplet set having different concentrations of the substance-of-interest. Adjusting the respective concentration of a corresponding sample droplet also includes combining a select number of the droplets from the droplet set to form an output droplet having a modified concentration. The select number of the droplets is based on the respective concentration of the corresponding sample droplet and the target concentration.

In some aspects, the method also includes performing an assay using the output droplet and the other sample droplets or outlet droplets that are based on the other sample droplets. Optionally, the assay is a sequencing-by-synthesis assay.

In some aspects, the method also includes identifying the select number of the droplets to be combined based on a dilution fraction (DF). The DF is equal to $(C_O \times k \times 2^d) \div C_I$; wherein d is the number of dilution operations, k is the number of droplets to be combined to form the output droplet, $C_I$ is the respective concentration of the sample droplet, and $C_O$ is the target concentration.

Optionally, identifying the select number of the droplets to be combined includes: (a) identifying an integer that is approximately equal to the DF and converting the integer into an n-bit binary number, wherein n is the number of dilution droplets available for combining; (b) counting a number of active digits in the n-bit binary number; (c) determining whether the number of active digits is equal to k. If the number of active digits is equal to k, the method includes correlating the active digits of the n-bit binary number to the droplets in the droplet set thereby identifying the droplets to be combined. If the number of active digits does not equal k, the method includes repeating (a)-(c) for a different integer.

In some aspects, the method also includes identifying the select number of the droplets to be combined using a lookup table. The lookup table includes a range of designated concentrations for the sample droplet. Optionally, the lookup table also includes at least one of (a) a range of numbers that represent the number of dilution operations that can be performed; (b) a range of numbers that represent the number of droplets available for combining; or (c) a range of numbers that represent the number of droplets to be combined together to form the output droplet. Optionally, the lookup table is populated based on a dilution fraction (DF). The DF is equal to $(C_O \times k \times 2^d) \div C_I$; wherein d is the number of dilution operations, k is the number of droplets to be combined to form the output droplet, $C_I$ is the respective concentration of the sample droplet, and $C_O$ is the targeted concentration.

In some aspects, the method also includes receiving user inputs that designate at least one of (a) a number of times dilution is performed; (b) a number of droplets available for combining; (c) a number of droplets to be combined to form the output droplet; (d) the respective concentration of the sample droplet; or (e) the target concentration.

In some aspects, the method also includes determining the target concentration. Determining the target concentration may include identifying the lowest respective concentration among the sample droplets. The target concentration may be based on the lowest respective concentration. Determining the target concentration may also include receiving user inputs that identify the target concentration. Determining the target concentration may also include receiving user inputs that confirm a suggested target concentration.

Optionally, the method also includes combining the output droplet with other sample droplets and/or other output droplets that are based on the other sample droplets, thereby forming a sample pool. Optionally, the method also includes performing an assay using the sample pool.

In an embodiment, a system is provided that includes a droplet actuator having a droplet-operations gap and a plurality of electrodes positioned along the droplet-operations gap. The droplet actuator is configured to receive discrete sample droplets in the droplet-operations gap. The system also includes a controller operably coupled to the electrodes of the droplet actuator. The controller is configured to control the electrodes to determine respective concentrations of a substance-of-interest in the sample droplets. The controller is also configured to control the electrodes to adjust the respective concentration of at least one of the sample droplets so that each of the respective concentrations of at least a plurality of the sample droplets is substantially equal to a target concentration. Adjusting the respective concentration of a corresponding sample droplet includes conducting droplet operations within the droplet-operations gap using the electrodes to generate discrete dilution droplets that are formed from the corresponding sample droplet. The dilution droplets and a remainder of the corresponding sample droplet form a droplet set. At least two of the dilution droplets in the droplet set having different concentrations of the substance-of-interest. Adjusting the respective concentration of a corresponding sample droplet also includes combining a select number of the droplets from the droplet set to form an output droplet. The select number of the droplets is based on the concentration of the corresponding sample droplet and the target concentration.

In some aspects, the controller is configured to perform an assay using the output droplet and the other sample droplets or outlet droplets that are based on the other sample droplets. Optionally, the assay is a sequencing-by-synthesis assay.

In some aspects, each of the dilution droplets is formed by combining a first volume of a dilution liquid and a second volume of another droplet. The other droplet is the sample droplet or one of the other dilution droplets. Optionally, the first and second volumes are equal volumes such that the concentration of each dilution droplet is about half the concentration of the other droplet.

In some aspects, the dilution droplets that are selected to be combined are based on at least one of (a) a designated number of dilution operations; (b) a designated number of droplets available for combining; or (c) a designated number of droplets to be combined together to form the output droplet.

In some aspects, the controller is configured to identify the select number of the droplets to be combined based on a dilution fraction (DF). The DF is equal to $(C_O \times k \times 2^d) \div C_I$;

wherein d is the number of dilution operations, k is the number of droplets to be combined to form the output droplet, $C_I$ is the respective concentration of the sample droplet, and $C_O$ is the target concentration.

Optionally, identifying the select number of the droplets to be combined by the controller includes (a) identifying an integer that is approximately equal to the DF and converting the integer into an n-bit binary number, wherein n is the number of dilution droplets available for combining; (b) counting a number of active digits in the n-bit binary number; (c) determining whether the number of active digits is equal to k. If the number of active digits is equal to k, the controller is configured to correlate the active digits of the n-bit binary number to the droplets in the droplet set thereby identifying the droplets to be combined. If the number of active digits does not equal k, the controller is configured to repeat (a)-(c) for a different integer.

In some aspects, the controller is configured to identify the select number of the droplets to be combined using a lookup table. The lookup table includes a range of designated concentrations for the sample droplet. Optionally, the lookup table also includes at least one of: (a) a range of numbers that represent the number of dilution operations that can be performed; (b) a range of numbers that represent the number of droplets available for combining; or (c) a range of numbers that represent the number of droplets to be combined together to form the output droplet.

Optionally, the lookup table is populated based on a dilution fraction (DF). The DF is equal to $(C_O \times k \times 2^d) \div C_I$; wherein d is the number of dilution operations, k is the number of droplets to be combined to form the output droplet, $C_I$ is the respective concentration of the sample droplet, and $C_O$ is the targeted concentration.

In some aspects, the controller is configured to receive user inputs that designate at least one of (a) a number of times dilution is performed; (b) a number of droplets available for combining; (c) a number of droplets to be combined to form the output droplet; (d) the respective concentration of the sample droplet; or (e) the target concentration.

In some aspects, the controller is configured to determine the target concentration. Determining the target concentration may include identifying the lowest respective concentration among the sample droplets. The target concentration being based on the lowest respective concentration. Determining the target concentration may include receiving user inputs that identify the target concentration. Determining the target concentration may include receiving user inputs that confirm a suggested target concentration. Optionally, the controller is configured to combine the output droplet with other sample droplets and/or other output droplets that are based on the other sample droplets, thereby forming a sample pool. Optionally, the controller is configured to perform an assay using the sample pool.

The foregoing detailed description of embodiments refers to the accompanying drawings, which illustrate specific embodiments of the present disclosure. Other embodiments having different structures and operations do not depart from the scope of the present disclosure. It will be understood that various details may be changed without departing from the scope. Furthermore, the foregoing description is for the purpose of illustration only, and not for the purpose of limitation.

The following claims recite certain embodiments of the present application. The language of the claims is hereby incorporated into the Detailed Description.

What is claimed:

1. A method comprising:
    providing a droplet actuator having a droplet-operations gap and a plurality of electrodes positioned along the droplet-operations gap;
    positioning an input droplet in the droplet-operations gap, the input droplet having a starting concentration of a substance-of-interest;
    conducting droplet operations within the droplet-operations gap using the electrodes to generate discrete dilution droplets that are formed from the input droplet, wherein the dilution droplets and a remainder of the input droplet form a droplet set, at least two of the dilution droplets in the droplet set having different concentrations of the substance-of-interest; and
    combining a select number of the droplets from the droplet set to form an output droplet having a modified concentration that is substantially equal to a designated target concentration.

2. The method of claim 1, wherein each of the dilution droplets is formed by combining a first volume of a dilution liquid and a second volume of another droplet, the other droplet being the input droplet or one of the other dilution droplets.

3. The method of claim 2, wherein the first and second volumes are equal volumes such that the concentration of each dilution droplet is about half the concentration of the other droplet.

4. The method of claim 1, wherein the dilution droplets that are selected to be combined are based on at least one of: (a) a designated number of dilution operations; (b) a designated number of droplets available for combining; (c) a designated number of droplets to be combined together to form the output droplet; (d) the starting concentration of the input droplet; or (e) the target concentration of the output droplet.

5. The method of claim 1, further comprising identifying the select number of the droplets to be combined based on a dilution fraction (DF), the DF being equal to:

$(C_O \times k \times 2^d) \div C_I$;

wherein d is the number of dilution operations, k is the number of droplets to be combined to form the output droplet, $C_I$ is the concentration of the input droplet, and $C_O$ is the target concentration of the output droplet.

6. The method of claim 5, wherein identifying the select number of droplets to be combined includes:
    (a) identifying an integer that is approximately equal to the DF and converting the integer into an n-bit binary number, wherein n is the number of dilution droplets available for combining;
    (b) counting a number of active digits in the n-bit binary number;
    (c) determining whether the number of active digits is equal to k;
    wherein, if the number of active digits is equal to k, the method includes correlating the active digits of the n-bit binary number to the droplets in the droplet set thereby identifying the droplets to be combined;
    wherein, if the number of active digits does not equal k, the method includes repeating (a)-(c) for a different integer.

7. The method of claim 1, further comprising identifying the select number of the droplets to be combined using a lookup table, the lookup table including (a) a range of designated concentrations for the input droplet and (b) a range of designated concentrations for the output droplet.

8. The method of claim 7, wherein the lookup table also includes at least one of: (a) a range of numbers that represent the number of dilution operations that can be performed; (b) a range of numbers that represent the number of droplets available for mixing; (c) a range of numbers that represent the number of droplets to be combined together to form the output droplet.

9. The method of claim 8, wherein the lookup table is populated based on a dilution fraction (DF), the DF being equal to:

$$(C_O \times k \times 2^d) \div C_I;$$

wherein d is the number of dilution operations, k is the number of droplets to be combined together to form the output droplet, $C_I$ is the concentration of the input droplet, and $C_O$ is the target concentration of the output droplet.

10. The method of claim 1, further comprising receiving user inputs that designate at least one of (a) a number of times dilution is performed; (b) a number of droplets available for mixing; (c) a number of droplets to be combined together to form the output droplet; (d) the starting concentration of the input droplet; or (e) the target concentration of the output droplet.

11. The method of claim 1, further comprising determining the target concentration by at least one of receiving user inputs about the input droplet or analyzing the input droplet on the droplet actuator.

12. A system comprising:
a droplet actuator having a droplet-operations gap and a plurality of electrodes positioned along the droplet-operations gap, the droplet-operations gap configured to receive an input droplet, the input droplet having a starting concentration of a substance-of-interest; and
a controller operably coupled to the electrodes of the droplet actuator, the controller configured to control the electrodes to:
conduct droplet operations within the droplet-operations gap using the electrodes to generate discrete dilution droplets that are formed from the input droplet, wherein the dilution droplets and a remainder of the input droplet form a droplet set, at least two of the dilution droplets in the droplet set having different concentrations of the substance-of-interest; and
combining a select number of the droplets from the droplet set to form an output droplet, the output droplet having a modified concentration of the substance-of-interest that is substantially equal to a designated target concentration.

13. The system of claim 12, wherein the modified concentration is substantially equal to the target concentration if the modified concentration is within 30% of the target concentration.

14. The system of claim 12, wherein the system is configured to perform a library preparation assay using the output droplet.

15. A method comprising:
loading sample droplets into a droplet actuator, the droplet actuator having a droplet-operations gap and a plurality of electrodes positioned along the droplet-operations gap, the sample droplets being separated from one another in the droplet-operations gap and including a substance-of-interest; and
determining respective concentrations of the substance-of-interest in the sample droplets;
adjusting the respective concentration of at least one of the sample droplets so that each of the respective concentrations of at least a plurality of the sample droplets is substantially equal to a target concentration, wherein adjusting the respective concentration of a corresponding sample droplet includes:
conducting droplet operations within the droplet-operations gap using the electrodes to generate discrete dilution droplets that are formed from a corresponding sample droplet, wherein the dilution droplets and a remainder of the corresponding sample droplet form a droplet set, at least two of the dilution droplets in the droplet set having different concentrations of the substance-of-interest;
combining a select number of the droplets from the droplet set to form an output droplet having a modified concentration, the select number of the droplets being based on the respective concentration of the corresponding sample droplet and the target concentration.

16. The method of claim 15, wherein the substance-of-interest comprises nucleic acids.

17. The method of claim 16, further comprising performing a sequencing-by-synthesis assay using the output droplet and the other sample droplets or outlet droplets that are based on the other sample droplets.

18. The method of claim 16, wherein the sample droplets are from different sources, the nucleic acids of each sample droplet being tagged to indicate the corresponding source.

19. The method of claim 15, further comprising determining the target concentration, wherein determining the target concentration includes identifying the lowest respective concentration among the sample droplets, the target concentration being based on the lowest respective concentration.

20. The method of claim 15, further comprising determining the target concentration, wherein determining the target concentration includes receiving user inputs that confirm a suggested target concentration.

* * * * *